United States Patent [19]

Findeisen et al.

[11] Patent Number: 5,166,356
[45] Date of Patent: Nov. 24, 1992

[54] SUBSTITUTED TRIAZOLINONE HERBICIDES AND PLANT GROWTH REGULATORS

[75] Inventors: Kurt Findeisen, Odenthal; Markus Lindig, Hilden; Hans-Joachim Santel, Leverkusen; Robert R. Schmidt; Klaus Lürssen, both of Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 741,702

[22] Filed: Aug. 6, 1991

Related U.S. Application Data

[62] Division of Ser. No. 168,823, Mar. 16, 1988, Pat. No. 5,061,311.

[30] Foreign Application Priority Data

Mar. 24, 1987 [DE] Fed. Rep. of Germany ....... 3709574

[51] Int. Cl.⁵ .......................................... C07D 249/12
[52] U.S. Cl. ............................... 548/263.8; 548/263.4
[58] Field of Search ........................... 548/263.4, 263.8

[56] References Cited

U.S. PATENT DOCUMENTS 4,931,084 6/1990 Findeisen et al. ................ 548/263.4

*Primary Examiner*—Patricia L. Morris
*Attorney, Agent, or Firm*—Sprung Horn Kramer & Woods

[57] ABSTRACT

Novel herbicides and plant growth regulants of the formula

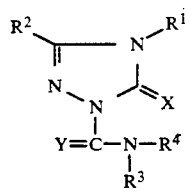

in which
$R^1$ represents hydrogen, alkyl, alkenyl, alkinyl, halogenoalkyl, halogenoalkenyl, halogenoalkinyl, alkoxyalkyl, alkoxy, cycloalkylalkyl or cycloalkyl, or represents in each case optionally substituted aralkyl or aryl,
$R^2$ represents a radical

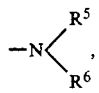

or represents a radical $—S(O)_n—R^7$,
$R^3$ and $R^4$ independently of one another each represent hydrogen, alkyl, alkenyl, alkinyl, halogenoalkyl, halogenoalkenyl, halogenoalkinyl, cyanoalkyl, hydroxyalkyl, alkoxyalkyl, alkylaminoalkyl, alkoxycarbonylalkyl or alkoxycarbonylalkenyl, or represent in each case optionally substituted cycloalkyl, cycloalkylalkyl, cycloalkenyl or cycloalkenylalkyl, or represent optionally substituted heterocyclylalkyl, or represent in each case optionally substituted aralkyl, aroyl, or aryl, or represent alkoxy, alkenyloxy, alkinyloxy, aralkyloxy or aryloxy, or, together with the nitrogen atom to which they are bonded, represent an optionally substituted heterocyclic radical, p0 X represents oxygen or sulphur and p0 Y represents oxygen or sulphur, wherein
$R^5$ and $R^6$ independently of one another each represent alkyl, alkenyl, alkinyl, halogenoalkyl, halogenoalkenyl, halogenoalkinyl, alkoxyalkyl, alkoxy, cycloalkyl or cycloalkylalkyl, or represent in each case optionally substituted aryl, aralkyl or heteroaryl, or, together with the nitrogen atom to which they are bonded, represent an optionally substituted heterocyclic radical,
$R^7$ represents alkyl, alkenyl, cycloalkyl or cycloalkylalkyl, or represents in each case optionally substituted aralkyl or aryl and
n represents the number 0, 1 or 2,
but wherein $R^2$ only represents a radical $—S(O)_n—R^7$ if $R^3$ and $R^4$ do not simultaneously represent methyl.

Intermediates therefor where $NR^3R^4$ is replaced by Cl are also new.

3 Claims, No Drawings

SUBSTITUTED TRIAZOLINONE HERBICIDES AND PLANT GROWTH REGULATORS

This is a division of application Ser. No. 168,823 filed Mar. 16, 1988, now U.S. Pat. No. 5,061,311.

The invention relates to new substituted triazolinones, several processes for their preparation and their use as herbicides and plant growth regulators.

It is known that certain nitrogen-heterocyclics, such as, for example, imidazolidin-2-one-1-carboxylic acid isobutylamide (compare, for example, K.H. Büchel "Pflanzenschutz and Schädlingsbekämpfung" ("Plant Protection and Pest Control") page 170, Thieme Verlag Stuttgart 1977) or 1-phenyl-3-(3-trifluoromethylphenyl)-5-methylperhydropyrimidin-2-one (compare, for example, European Patent 58,868 or DE-OS (German Published Specification) 3,237,479) have herbicidal properties.

However, the herbicidal activity of these already known compounds against problem weeds, like their tolerance towards important crop plants, is not always completely satisfactory in all fields of use.

Certain substituted triazolinones, such as, for example, 1-(N,N-dimethylcarbamoyl)-3-isopropylthio-4-methyl-1,2,4-triazoline-5-thione, 1-(N,N-dimethylcarbamoyl)-3-ethylthio-4-methyl-1,2,4-triazoline-5-thione, 1-(N,N-dimethylcarbamoyl)-3-isopropylthio-4-methyl-1,2,4-triazolin-5-one, 1-(N,N-dimethylcarbamoyl)-3-ethylthio-4-methyl-1,2,4-triazolin-5-one, 1-(N,N-dimethylcarbamoyl)-3-methylthio-4-methyl-1,2,4-triazolin-5-one, 1(N,N-dimethylcarbamoyl)-3-propylthio-4-methyl-1,2,4-triazoline-5-thione, 1-(N,N-dimethylcarbamoyl)-3-allylthio-4-methyl-1,2,4-triazoline-5-thione and 1-(N,N-dimethylcarbamoyl)-3-methylthio-4-methyl-1,2,4-triazoline-5-thione, are furthermore known (compare DE-OS (German Published Specification) 2,707,801). Nothing is as yet known of an activity of these already known triazolinones as herbicides or plant growth regulators.

New substituted triazolinones of the general formula (I)

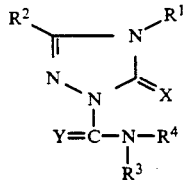

in which $R^1$ represents hydrogen, alkyl, alkenyl, alkinyl, halogenoalkyl, halogenoalkenyl, halogenoalkinyl, alkoxyalkyl, alkoxy, cycloalkylalkyl or cycloalkyl, or represents in each case optionally substituted aralkyl or aryl, $R^2$ represents a radical

or represents a radical $-S(O)_n-R^7$, $R^3$ and $R^4$ independently of one another each represent hydrogen, alkyl, alkenyl, alkinyl, halogenoalkyl, halogenoalkenyl, halogenoalkinyl, cyanoalkyl, hydroxyalkyl, alkoxyalkyl, alkylaminoalkyl, alkoxycarbonylalkyl or alkoxycarbonylalkenyl, or represent in each case optionally substituted cycloalkyl, cycloalkylalkyl, cycloalkenyl or cycloalkenylalkyl, or represent optionally substituted heterocyclylalkyl, or represent in each case optionally substituted aralkyl, aroyl or aryl, or represent alkoxy, alkenyloxy, alkinyloxy, aralkyloxy or aryloxy, or, together with the nitrogen atom to which they are bonded, represent an optionally substituted heterocyclic radical, X represents oxygen or sulphur and Y represents oxygen or sulphur, wherein $R^5$ and $R^6$ independently of one another each represent alkyl, alkenyl, alkinyl, halogenoalkyl, halogenoalkenyl, halogenoalkinyl, alkoxyalkyl, alkoxy, cycloalkyl or cycloalkylalkyl, or represent in each case optionally substituted aryl, aralkyl or heteroaryl, or, together with the nitrogen atom to which they are bonded, represent an optionally substituted heterocyclic radical, $R^7$ represents alkyl, alkenyl, alkinyl, cycloalkyl or cycloalkylalkyl, or represents in each case optionally substituted aralkyl or aryl and n represents the number 0, 1 or 2, but wherein $R^2$ only represents a radical $-S(O)_n-R^7$ if $R^3$ and $R^4$ do not simultaneously represent methyl, have been found.

It has furthermore been found that the new substituted triazolinones of the general formula (I)

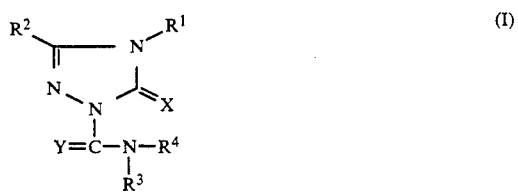

in which $R^1$, $R^2$, $R^3$, $R^4$, X and Y have the abovementioned meaning, are obtained by a process in which a) 1-chloro-(thio)-carbonyltriazolinones of the formula (II)

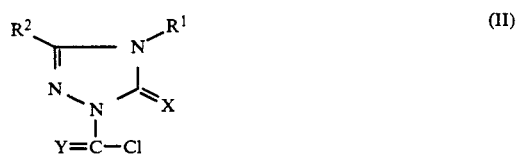

in which $R^1$, $R^2$, X and Y have the abovementioned meaning, are reacted with amines of the formula (III)

in which $R^3$ and $R^4$ have the abovementioned meaning, if appropriate in the presence of a diluent and if appropriate in the presence of an acid-binding agent, or b) in the case where $R^3$ denotes hydrogen, by a process in which triazolinones unsubstituted in the 1-position, of the formula (IV)

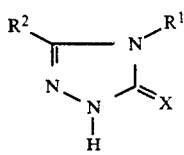

in which $R^1$, $R^2$ and X have the abovementioned meaning, are reacted with iso(thio)cyanates of the formula (V)

$$R^4-N=C=Y \qquad (V)$$

in which $R^4$ and Y have the abovementioned meaning, if appropriate in the presence of a diluent and if appropriate in the presence of a reaction auxiliary.

Finally, it has been found that the new substituted triazolinones of the general formula (I) have herbicidal and growth-regulating properties.

Surprisingly, the substituted triazolinones of the general formula (I) according to the invention exhibit a considerably higher herbicidal potency against problem weeds than the nitrogen-heterocyclics known from the prior art, such as, for example, imidazolin-2-one-1-carboxylic acid isobutylamide or 1-phenyl-3-(3-trifluoromethylphenyl)-5-methyl-perhydropyrimidin-2-one, which are closely related compounds chemically and from the point of view of their action and moreover also have growth-regulating properties.

Formula (I) provides a general definition of the substituted triazolinones according to the invention. Preferred compounds of the formula (I) are those in which
$R^1$ represents hydrogen, or represents in each case straight-chain or branched alkyl with 1 to 8 carbon atoms, alkenyl with 2 to 8 carbon atoms, alkinyl with 2 to 8 carbon atoms, halogenoalkyl with 1 to 8 carbon atoms and 1 to 17 identical or different halogen atoms, halogenoalkenyl with 2 to 8 carbon atoms and 1 to 15 identical or different halogen atoms, halogenoalkinyl with 2 to 8 carbon atoms and 1 to 13 identical or different halogen atoms or alkoxyalkyl or alkoxy with in each case 1 to 6 carbon atoms in the individual alkyl parts, or represents cycloalkylalkyl or cycloalkyl with in each case 3 to 7 carbon atoms in the cycloalkyl part and if appropriate 1 to 6 carbon atoms in the straight-chain or branched alkyl part, or represents aralkyl or aryl with in each case 6 to 10 carbon atoms in the aryl part and where appropriate 1 to 6 carbon atoms in the straight-chain or branched alkyl part, in each case optionally monosubstituted or polysubstituted by identical or different substituents, possible substituents on the aryl being: halogen, cyano, nitro and in each case straight-chain or branched alkyl, alkoxy, alkylthio, halogenoalkyl, halogenoalkoxy and halogenoalkylthio with in each case 1 to 4 carbon atoms and where appropriate 1 to 9 identical or different halogen atoms,
$R^2$ represents a radical

or represents a radical $-S(O)_n-R^7$,
$R^3$ and $R^4$ independently of one another each represent hydrogen, or represent in each case straight-chain or branched alkyl with 1 to 18 carbon atoms, alkenyl with 2 to 8 carbon atoms, alkinyl with 2 to 8 carbon atoms, halogenoalkyl with 1 to 8 carbon atoms and 1 to 17 identical or different halogen atoms, halogenoalkenyl or halogenoalkinyl with in each case 2 to 8 carbon atoms and 1 to 15 or 13 identical or different halogen atoms, cyanoalkyl with 1 to 8 carbon atoms, hydroxyalkyl with 1 to 8 carbon atoms and 1 to 6 hydroxyl groups, alkoxyalkyl, alkoxycarbonylalkyl or alkoxycarbonylalkenyl with in each case up to 6 carbon atoms in the individual alkyl or alkenyl parts, or alkylaminoalkyl or dialkylaminoalkyl with in each case 1 to 6 carbon atoms in the individual alkyl parts, or represents cycloalkyl, cycloalkylalkyl, cycloalkenyl or cycloalkenylalkyl with in each case 3 to 8 carbon atoms in the cycloalkyl or cycloalkenyl part and where appropriate 1 to 6 carbon atoms in the alkyl part, in each case optionally monosubstituted or polysubstituted by identical or different substituents, possible substituents in each case being halogen, cyano and in each case straight-chain or branched alkyl and halogenoalkyl with in each case 1 to 4 carbon atoms and where appropriate 1 to 9 identical or different halogen atoms, and in each case divalent alkanediyl or alkenediyl with in each case up to 4 carbon atoms; or furthermore represent heterocyclylalkyl which has 1 to 6 carbon atoms in the straight-chain or branched alkyl part and 1 to 9 carbon atoms as well as 1 to 3 hetero atoms—in particular nitrogen, oxygen and/or sulphur—in the heterocyclyl part and is optionally monosubstituted or polysubstituted in the heterocyclyl part by identical or different substituents, possible substituents being: halogen, cyano, nitro and in each case straight-chain or branched alkyl, alkoxy, alkylthio, halogenoalkyl, halogenoalkoxy, halogenoalkylthio and alkoxycarbonyl with in each case 1 to 5 carbon atoms and where appropriate 1 to 9 identical or different halogen atoms; or furthermore represent in each case straight-chain or branched alkoxy with 1 to 8 carbon atoms, alkenyloxy with 2 to 8 carbon atoms or alkinyloxy with 2 to 8 carbon atoms, or, finally, represent aralkyl, aralkyloxy, aryloxy, aroyl or aryl with in each case 6 to 10 carbon atoms in the aryl part and where appropriate 1 to 6 carbon atoms in the alkyl part, in each case optionally mono-substituted or polysubstituted by identical or different substituents, possible substituents on the aryl in each case being: halogen, cyano, nitro, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalylsulphonyl, alkanoyl and alkoxycarbonyl with in each case 1 to 6 carbon atoms and where appropriate 1 to 9 identical or different halogen atoms, cycloalkyl with 3 to 6 carbon atoms and phenoxy, and, where appropriate, possible substituents on the alkyl being: halogen and cyano, or
$R^3$ and $R^4$, together with the nitrogen atom to which they are bonded, represent a five- to ten-membered heterocyclic radical which can optionally contain 1 or 2 further hetero atoms, in particular nitrogen, oxygen and/or sulphur, and is optionally monosubstituted or polysubstituted by identical or different substituents, possible substituents being halogen and in each case straight-chain or branched alkyl or halogenoalkyl with in each case 1 to 4 carbon atoms and where appropriate 1 to 9 identical or different halogen atoms, as well as 1 or 2 oxo or thiono groups, X represents oxygen or sulphur and Y represents oxygen or sulphur, wherein $R^5$ and $R^6$ independently of one another each represent in each case straight-chain or branched alkyl with 1 to 8 carbon atoms, alkenyl with 2 to 8 carbon atoms, alkinyl with 2 to 8 carbon atoms, halogenoalkyl with 1 to 8 carbon atoms and 1 to 17 identical or different halogen atoms, halogenoalkenyl or halogenoalkinyl with in each case 2 to 8 carbon atoms and 1 to 15 or 13 identical or different halogen atoms or alkoxyalkyl or alkoxy with in each case 1 to 6 carbon atoms in the individual alkyl parts, or represent cycloalkyl with 3 to 7 carbon atoms, or represent cycloalkylalkyl with 3 to 7 carbon atoms in the cycloalkyl part and 1 to 6 carbon atoms in the alkyl part, or represent aralkyl with 6 to 10 carbon atoms in the aryl part and 1 to 6 carbon atoms in the alkyl part, aryl with 6 to 10 carbon atoms or heteroaryl with 2 to 9 carbon atoms and 1 to 3 hetero atoms, in particular nitrogen, oxygen and/or sulphur, in each case optionally monosubstituted or polysubstituted by identical or different substituents, possible substituents in each case being halogen, cyano, nitro and in each case straight-chain or branched alkyl, alkoxy, alkylthio, halogenoalkyl, halogenoalkoxy or halogenoalkylthio with in each case 1 to 4 carbon atoms and where appropriate 1 to 9 identical or different halogen atoms, or $R^5$ and $R^6$, together with the nitrogen atom to which they are bonded, represent a five- to ten-membered heterocyclic radical which can optionally contain 1 or 2 further hetero atoms, in particular nitrogen, oxygen and/or sulphur, and is optionally monosubstituted or polysubstituted by identical or different substituents, possible substituents being: halogen and in each case straight-chain or branched alkyl or halogenoalkyl with in each case 1 to 4 carbon atoms and where appropriate 1 to 9 identical or different halogen atoms, as well as 1 or 2 oxo or thiono groups, $R^7$ represents in each case straight-chain or branched alkyl with 1 to 8 carbon atoms, alkenyl with 2 to 8 carbon atoms or alkinyl with 2 to 8 carbon atoms, or represents cycloalkyl with 3 to 7 carbon atoms, or represents cycloalkylalkyl with 3 to 7 carbon atoms in the cycloalkyl part and 1 to 6 carbon atoms in the alkyl part, or represents aralkyl with 6 to 10 carbon atoms in the aryl part and 1 to 6 carbon atoms in the alkyl part or aryl with 6 to 10 carbon atoms, in each case optionally monosubstituted or polysubstituted by identical or different substituents, possible substituents on the aryl in each case being: halogen, cyano, nitro and in each case straight-chain or branched alkyl, alkoxy and halogenoalkyl with in each case 1 to 4 carbon atoms and where appropriate 1 to 9 identical or different halogen atoms, and n represents the number 0, 1 or 2, but wherein $R^2$ only represents a radical $-S(O)_n-R^7$ if $R^3$ and $R^4$ do not simultaneously represent methyl.

Particularly preferred compounds of the formula (I) are those in which $R^1$ represents hydrogen, methyl, ethyl, n- or i-propyl, n-, i-, s- or t-butyl, n- or i-pentyl, n- or i-hexyl, allyl, propargyl, methoxy, ethoxy or methoxymethyl, or represents straight-chain or branched halogenoalkyl with 1 to 4 carbon atoms and 1 to 9 identical or different halogen atoms, in particular fluorine, chlorine or bromine, or represents cyclopentyl, cyclohexyl, cyclopropyl, cyclopropylmethyl, cyclohexylmethyl or cyclohexylethyl, or represents phenyl or benzyl, in each case optionally substituted by one to three identical or different substituents, possible substituents being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy and trifluoromethylthio, $R^2$ represents a radical

or represents a radical $-S(O)_n-R^7$, $R^3$ and $R^4$ independently of one another each represent hydrogen, methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl, n- or i-dodecyl, allyl, n- or i-butenyl, n- or i-pentenyl, n- or i-hexenyl, propargyl, n- or i-butinyl, n- or i-pentinyl, n- or i-hexinyl, or represent straight-chain or branched halogenoalkyl with 1 to 6 carbon atoms and 1 to 9 identical or different halogen atoms, in particular fluorine, chlorine or bromine, or represent in each case straight-chain or branched halogenoalkenyl or halogenoalkinyl with in each case 3 to 5 carbon atoms and 1 to 3 halogen atoms, in particular fluorine or chlorine, or represent in each case straight-chain or branched cyanoalkyl with 1 to 6 carbon atoms in the alkyl part, hydroxyalkyl with 1 to 6 carbon atoms and 1 to 3 hydroxyl groups, alkoxyalkyl, alkoxycarbonylalkyl or alkoxycarbonylalkenyl, or alkylaminoalkyl or dialkylaminoalkyl with in each case up to 4 carbon atoms in the individual alkyl and alkenyl parts, or represent cyclopropyl, cyclopropylmethyl, cyclopropylethyl, cyclopentyl, cyclohexyl, cycloheptyl, cyclooctyl, cyclohexylmethyl, cyclohexylethyl, cyclohexenyl or cyclohexenylmethyl, in each case optionally substituted by one to three identical or different substituents, possible substituents in each case being: fluorine, chlorine, bromine, methyl, ethyl, n- or i-propyl, n-, i-, s- or t-butyl, cyano, methanediyl, ethanediyl, butanediyl and butadienediyl; or furthermore represent heterocyclylmethyl, heterocyclylpropyl or heterocyclylethyl, optionally substituted in the heterocyclyl part by one to three identical or different substituents, possible heterocyclic radicals in each case being:

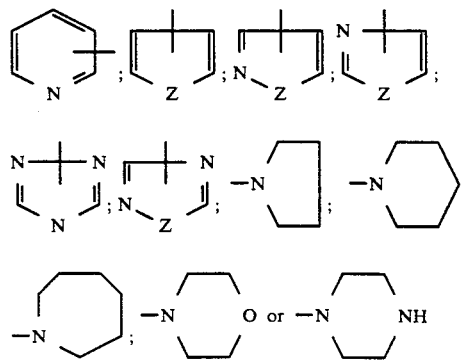

wherein

Z in each case represents oxygen or sulphur, and possible substituents being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy and trifluoromethylthio; or represent in each case straight-chain or branched alkoxy with 1 to 6 carbon atoms, alkenyloxy with 3 to 6 carbon atoms or alkinyloxy with 3 to 6 carbon atoms, or represent benzyl, phenylethyl, phenylpropyl, phenylbutyl, phenylpentyl, phenylhexyl, phenylheptyl, phenylcyanomethyl, phenylcyanoethyl, phenylcyanopropyl, benzyloxy, phenylethyloxy, phenoxy, benzoyl, phenyl or naphthyl, in each case optionally substituted by one to three identical or different substituents and where appropriate straight-chain or branched, possible substituents on the phenyl in each case being fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl and phenoxy; or $R^3$ and $R^4$, together with the nitrogen atom to which they are bonded, represent a heterocyclic radical of the formula

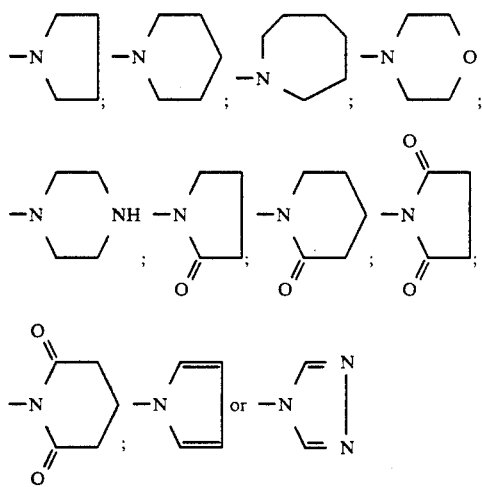

optionally substituted by one to three identical or different substituents, possible substituents being: methyl, ethyl, n- or i-propyl, chlorine and trifluoromethyl, X represents oxygen or sulphur and
Y represents oxygen or sulphur,
wherein
$R^5$ and $R^6$ independently of one another each represent methyl, ethyl, n- or i-propyl, n-, i-, s- or t-butyl, n- or i-pentyl, allyl or propargyl, or represent in each case straight-chain or branched halogenoalkyl with 1 to 4 carbon atoms, halogenoalkenyl with 3 to 6 carbon atoms or halogenoalkinyl with 3 to 6 carbon atoms and in each case 1 to 9 identical or different halogen atoms, or represent methoxymethyl, methoxyethyl, methoxy or ethoxy, or represent cyclopropyl, cyclopropylmethyl, cyclopentyl, cyclohexyl, cyclohexylmethyl, cyclohexylethyl or cyclopentylmethyl, or represent benzyl, phenethyl or phenyl, in each case optionally substituted by one to three identical or different substituents, possible substituents being: fluorine, chlorine, bromine, cyano, nitro, methyl, ethyl n- or i-propyl n-, i-, s- or t-butyl, methoxy, ethoxy, methylthio, trifluoromethyl, trifluoromethoxy and trifluoromethylthio, or $R^5$ and $R^6$, together with the nitrogen atom to which they are bonded, represent a heterocyclic radical of the formula

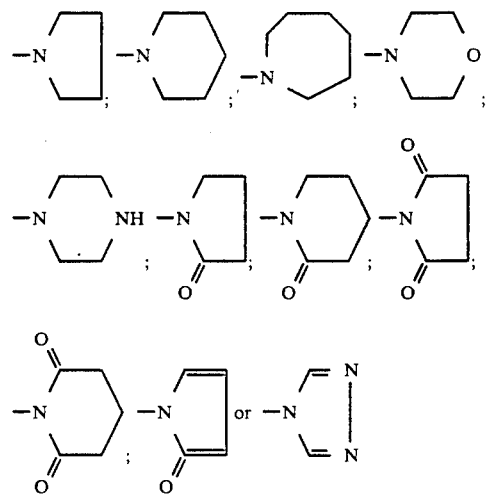

optionally substituted by one to three identical or different substituents, possible substituents being: methyl, ethyl, n- or i-propyl, chlorine and trifluoromethyl, $R^7$ represents methyl, ethyl, n- or i-propyl, n-, i-, s- or t-butyl, allyl, propargyl, cyclopentyl, cyclohexyl, cyclohexylmethyl or cyclohexylethyl, or represents benzyl or phenyl, in each case optionally substituted by one to three identical or different substituents, possible substituents in each case being: fluorine, chlorine, bromine, cyano, nitro, methyl, ethyl, n- or i-propyl, n-, i-, s- or t-butyl, methoxy, ethoxy and trifluoromethyl, and n represents the number 0, 1 or 2,
but wherein $R^2$ only represents a radical —S(O)$_n$—$R^7$ if $R^3$ and $R^4$ do not simultaneously represent methyl.

The compounds mentioned in the preparation examples may be mentioned specifically.

If, for example, 1-chlorocarbonyl-3-dimethylamino-4-methyl-1,2,4-triazolin-5-one and allylamine are used as starting substances, the course of the reaction in process (a) according to the invention can be represented by the following equation:

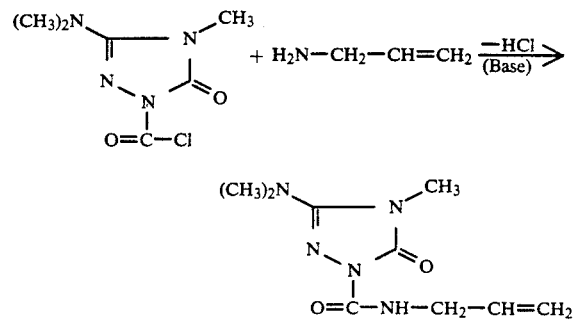

If, for example, 3-dimethylamino-4-methyl-1H-1,2,4-triazolin-5-one and isopropyl isocyanate are used as starting substances, the course of the reaction in process (b) according to the invention can be represented by the following equation:

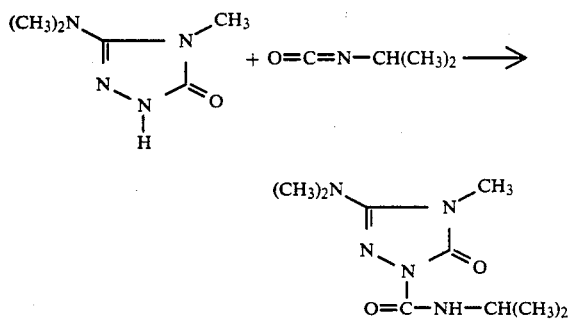

Formula (II) provides a general definition of the chloro(thio)carbonyl triazolinones required as starting substances for carrying out process (a) according to the invention. In this formula (II), $R^1$, $R^2$, X and Y preferably represent those radicals which have already been mentioned as preferred for these substituents in connection with the description of the substances of the formula (I) according to the invention.

The chloro(thio)carbonyl triazolinones of the formula (II) are not yet known.

They are obtained by a process in which triazolinones which are unsubstituted in the 1-position, of the formula (IV)

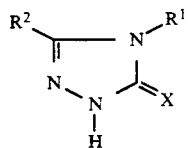 (IV)

in which $R^1$, $R^2$ and X have the abovementioned meaning, are reacted with (thio)phosgene of the formula (VI)

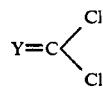 (VI)

in which Y has the abovementioned meaning, if appropriate in the presence of a diluent, such as, for example, toluene or acetonitrile, and if appropriate in the presence of an acid-binding agent, such as, for example, triethylamine, at temperatures between +20° C. and +150° C., and alternatively chloro(thio)carbonyl compounds of the formula (IIa)

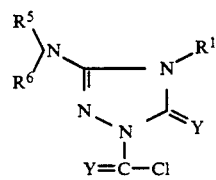 (IIa)

in which $R^1$, $R^5$, $R^6$ and Y have the abovementioned meaning, are also obtained by a process in which aminoguanidinium hydrochlorides of the formula (VII)

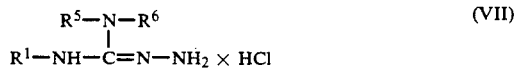 (VII)

in which $R^1$, $R^5$ and $R^6$ have the abovementioned meaning, are reacted with twice the molar excess of (thio)phosgene of the formula (VI)

 (VI)

in which Y has the abovementioned meaning, if appropriate in the presence of a diluent, such as, for example, toluene or acetonitrile, and if appropriate in the presence of an acid-binding agent, at temperatures between +20° C. and +150° C.

The aminoguanidinium hydrochlorides of the formula (VII) are obtained by a process analogous to known processes, for example by a procedure in which the generally known ureas of the formula (VIII)

 (VIII)

in which $R^1$, $R^5$ and $R^6$ have the abovementioned meaning, are initially reacted in a 1st stage with (thio)phosgene of the formula (VI)

 (VI)

in which Y has the abovementioned meaning, if appropriate in the presence of a diluent, such as, for example, toluene or acetonitrile, at temperatures between +10° C. and +150° C., and the formamidine hydrochlorides thus obtainable, of the formula (IX)

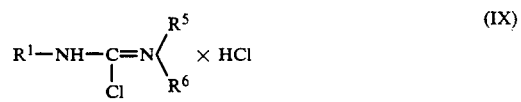 (IX)

in which $R^1$, $R^5$ and $R^6$ have the abovementioned meaning are reacted in a 2nd stage with hydrazine hydrate, if appropriate in the presence of a diluent, such as, for example, isopropanol or methylene chloride, at temperatures between −10° C. and +60° C. (compare, for example, J. org. Chem. 19, 1807 [1954]; Bull. Soc. Chim. Fr. 1975, 1649; and U.S. Pat. No. 2,845,458).

Ureas of the formula (VIII) and phosgene and thiophosgene of the formula (VI) are generally known compounds of organic chemistry.

Formula (III) provides a general definition of the amines furthermore required as starting substances for carrying out process (a) according to the invention. In this formula (III), $R^3$ and $R^4$ preferably represent those radicals which have already been mentioned as preferred for these substituents in connection with the description of the substances of the formula (I) according to the invention.

The amines of the formula (III) are generally known compounds of organic chemistry.

Formula (IV) provides a general definition of the triazolinones which are unsubstituted in the 1-position and are required as starting substances for carrying out process (b) according to the invention and for the synthesis of the precursors of the formula (II). In this formula (IV), $R^1$, $R^2$ and X preferably represent those radicals which have already been mentioned as preferred for these substituents in connection with the description of the substances of the formula (I) according to the invention.

The triazolinones of the formula (IV) which are unsubstituted in the 1-position are known in some cases (compare, for example, Chem. Ber. 102, 735 [1969]; Chem. Ber. 107, 454 [1974]; Arch. Pharm. 307, 509 [1974]; Helv. Chim. Acta 63, 841 [1980]; U.S. Pat. No. 4,098,896; U.S. Pat. No. 4,110,332; U.S. Pat. No. 4,530,898; DE-OS (German Published Specification) 2,250,572; J. chem. Soc. C. 1967, 746; J. Chem. Soc. Perkin Trans. I, 1059 [1982]; Arzneimittel Forsch. 27, 343 [1977]; Compt. Rend. 253, 1974 [1961]; Bull. Soc. Chim. Fr 1963, 144; and French Patent FR M 1,559 of 3.12.62). The known as well as the unknown compounds of the formula (IV) are obtained by a process analogous to known processes (compare, for example, J. org. Chem. 51, 1719 [1986]; U.S. Pat. No. 4,098,896 and the preparation examples). Triazolinones which are unsubstituted in the 1-position, of the formula (IVa)

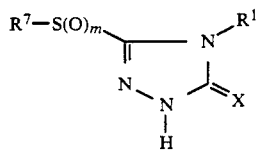

(IVa)

in which
$R^1$, $R^7$ and X have the abovementioned meaning and m represents the number 1 or 2,
are obtained from the corresponding compounds of the formula (IVb)

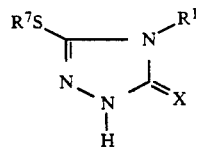

(IVb)

in which $R^1$, $R^7$ and X have the abovementioned meaning, in the generally known manner with customary oxidizing agents, for example by reaction with 3-chloroperbenzoic acid, if appropriate in the presence of a diluent, such as, for example, methylene chloride or acetonitrile, and if appropriate in the presence of a catalyst, such as, for example, ammonium molybdate, at temperatures between 0° C. and 40° C.

Formula (V) provides a general definition of the iso(thio)cyanates furthermore required as starting substances for carrying out process (b) according to the invention. In this formula (V), $R^4$ and Y preferably represent those radicals which have already been mentioned as preferred for these substituents in connection with the description of the substances of the formula (I) according to the invention.

The iso(thio)cyanates are generally known compounds of organic chemistry (compare, for example, Saul Patai, "The Chemistry of Cyanates and their Thio derivatives" J. Wiley & Sons, New York 1977).

Possible diluents for carrying out process (a) according to the invention are the inert organic solvents These include, in particular, aliphatic, alicyclic or aromatic, optionally halogenated hydrocarbons, such as, for example, benzine, ligroin, benzene, toluene, xylene, chlorobenzene, petroleum ether, pentane, hexane, heptane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methyl-formanilide, N-methylpyrrolidone or hexamethylphosphoric acid triamide, esters, such as ethyl acetate, or bases, such as pyridine.

If appropriate, process (a) according to the invention is carried out in the presence of a suitable acid-binding agent.

Possible acid-binding agents are all the customary inorganic or organic bases. These include, for example, alkali metal hydroxides, such as sodium hydroxide or potassium hydroxide, alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

It is also possible for the amine of the formula (III) used as the reaction partner to be used simultaneously as the acid-binding agent in an appropriate excess.

The reaction temperatures can be varied within a substantial range in carrying out process (a) according to the invention. The reaction is in general carried out at temperatures between 0° C. and +150° C., preferably at temperatures between +10° C. and +80° C.

Process (a) according to the invention is usually carried out under normal pressure. However, it is also possible for the process to be carried out under increased pressure.

For carrying out process (a) according to the invention, in general 1.0 to 5.0 mols preferably 1.0 to 2.5 mols of amine of the formula (III) and if appropriate 1.0 to 2.5 mols of acid-binding agent are employed per mol of 1-chloro-(thio)carbonyl-triazolinone of the formula (II). The reaction is carried out and the reaction products are worked up and isolated by a process analogous to generally known processes.

Possible diluents for carrying out process (b) according to the invention are likewise inert organic solvents. The diluents mentioned for process (a) are preferably used.

If appropriate, process (b) according to the invention can be carried out in the presence of a basic reaction auxiliary. Possible reaction auxiliaries are all the customary inorganic and organic bases. Bases which are preferably used are tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

However, it is not absolutely essential to add such catalysts.

The reaction temperatures can be varied within a substantial range in carrying out process (b) according to the invention. The reaction is in general carried out at temperatures between 0° C. and +150° C., preferably at temperatures between +40° C. and +120° C.

Process (b) according to the invention is usually carried out under normal pressure. However, it is also possible for the process to be carried out under increased pressure, especially in the case of gaseous starting compounds.

For carrying out process (b) according to the invention, in general 1.0 to 5.0 mols preferably 1.0 to 2.5 mols of iso(thio)cyanate of the formula (V) and if appropriate 1.0 to 2.5 mols of reaction auxiliary are employed per mol of triazolinone of the formula (IV) unsubstituted in the 1-position. The reaction is carried out and the reaction products are worked up and isolated by a process analogous to generally known processes.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera:

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera:

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera:

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera:

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can thereby be used with particularly good success for combating mono- and dicotyledon weeds, in particular in monocotyledon crops.

The active compounds according to the invention moreover engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

When applied in appropriate amounts, the active compounds according to the invention also exhibit an insecticidal, bactericidal and fungicidal activity and can be used, for example, for combating hygiene and pests of stored products or for combating fungal diseases in cereals and rice-growing, such as, for example, against the mildew of cereal causative organism (Erysiphe graminis) or against the rice spot disease causative organism (Pyricularia oryzae). In this field of use, the active compounds according to the invention also show systemic properties, in addition to good protective properties.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazin-2,4(1H, 3H)-dione or N-(2-benzothiazolyl)-N,N'-dimethylurea, for combating weeds in cereals; 4-amino-3-methyl-6-phenyl-1,2,4-triazin-5(4H)-one, for combating weeds in sugar beets and 4-amino-6-(1,1-dimethylethyl)-3-methylthio-1,2,4-triazin-5(4H )-one, for combating weeds in soy beans. Mixtures with N,N-dimethyl-N'-(3-chloro-4-methylphenyl)-urea; N,N-dimethyl-N'-(4-isopropylphenyl)-urea; 2-chloro-4-ethylamino-6-isopropylamino-1,3,5-triazine; 4-ethylamino-2-t-butylamino-6-methylthio-s-triazine; 2-chloro-4-ethylamino-6-(3-cyanopropylamino)-1,3,5-triazine; 4-amino-6-t-butyl-3-ethylthio-1,2,4-triazin-5(4H)-one; N-methyl-2-(1,3-benzothiazol-2-yloxy)-acetanilide; S-(2,3,3-trichloroallyl) N,N-diisoproyl-thiolcarbamate; 2-ethyl-6-methyl-N-(1-methyl-2-methoxyethyl)-chloroacetanilide; chloroacetic acid N-(methoxymethyl)-2,6-diethylanilide; 2-chloro-N-(2,6-dimethylphenyl)-N-[(1H)-pyrazol-1-ylmethyl]-acetamide; α-chloro-2', 6'-diethyl-N-(2-propoxyethyl)-acetanilide; 2-[5-methyl-5-(1-methylethyl)-4-oxo-2-imidazolin-2-yl]-3-quinolinecarboxylic acid; methyl 2-[4,5-dihydro-4-methyl-4-(1-methylethyl)-5-oxo-1H-imidazol-2-yl]-4(5) -methylbenzoate; methyl 5-(2,4-dichlorophenoxy)-2-nitrobenzoate; 5-(2-chloro-4-trifluoromethylphenoxy)-N-methylsulphonyl-2-nitrobenzamide; 2-ethoxy-1-methyl-2-oxo-ethyl 5-[2-chloro-4-(trifluoromethyl)-phenoxy]-2-nitrobenzoate; 5-(2-chloro-4-trifluoromethylphenoxy)-2-nitro-benzoic acid; 2,4-dichlorophenoxyacetic acid; 2,4-dichlorophenoxypropionic acid; 2-methyl-4-chlorophenoxyacetic acid; 4-chloro-2-methylphenoxypropionic acid; 3,5-diiodo-4-hydroxybenzonitrile; 3,5-dibromo-4-hydroxy-benzonitrile; 2-chloro-N-([(4-methoxy-6 methyl-1,3,5-triazin-2-yl)-amino]-carbonyl]-benzenesulphonamide; 2-{[[((4-methoxy-6-methyl-1,3,5-triazin-2-yl)-amino)-carbonyl]-amino]-sulphonyl}-benzoic acid or its methyl ester 2-{4-[(3-chloro-5-(trifluoromethyl)-2-pyridinyl)-oxy]-phenoxy}-propanoic acid or -propanoic acid ethyl ester; trimethylsilylmethyl 2-[4-(3,5-dichloropyrid-2-yloxy)-phenoxy]-propionate; 0-(6-chloro-3-phenyl-pyridazin-4-yl) S-octyl thiocarbonate and 3-isopropyl-2,1,3-benzothiadiazin-4-one 2,2-dioxide are also possible. Surprisingly, some mixtures also exhibit a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

When used as growth regulators, the active compounds according to the invention can likewise be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

The amounts thereby applied can likewise be varied within a substantial range. When used as growth regulators, 0.01 to 50 kg, preferably 0.05 to 10 kg, of active compound are generally used per hectare of soil surface.

As regards the time of application, the growth regulators are applied within a preferred period of time, the exact definition of which depends on the climatic and vegetative circumstances.

PREPARATION EXAMPLES

Example 1:

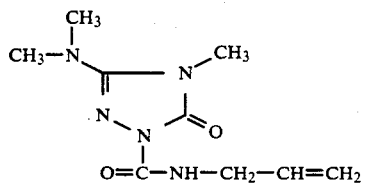

(Process a)

5.7 g (0.1 mol) of allylamine are added dropwise to 10.25 g (0.05 mol) of 1-chlorocarbonyl-3-dimethylamino-4-methyl-1,2,4-triazolin-5-one in 200 ml of acetonitrile, with stirring, such that the temperature does not rise above 40° C. When the addition has ended, the mixture is stirred at room temperature for four hours, the allylamine hydrochloride which has precipitated is then filtered off, the filtrate is concentrated in vacuo, the oily residue is taken up in 150 ml of methylene chloride, the mixture is washed three times with 50 ml of water each time and dried over sodium sulphate and the solvent is removed in vacuo.

8.8 g (79% of theory) of 1-allylaminocarbonyl-3-dimethylamino-4-methyl-1,2,4-triazolin-5-one are obtained as an oil.

$^1$H-NMR (CDCl$_3$/TMS) δ=4.0 (2H, CH$_2$); 5.8–6.0 (1H; CH=); 5.1–5.3 (2H; =CH$_2$) ppm.

Preparation of the starting compounds

Example II-1:

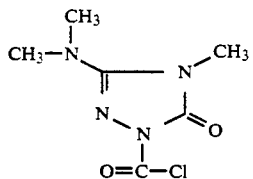

71 g (0.5 mol) of 3-dimethylamino-4-methyl-1H-1,2,4-triazolin-5-one in 300 ml of toluene are heated at 120° C., while passing in phosgene. A total of 115 g (1.15 mol) of phosgene are passed in. A vigorous evolution of hydrogen chloride takes place from 80° C. When the introduction of phosgene has ended, the mixture is stirred at 120° C. for a further 5 hours, excess phosgene and hydrogen chloride are removed by blowing out with nitrogen and the mixture is filtered at 20° C. The filtrate is stirred with 1 l of cyclohexane and the product which has precipitated is filtered off with suction, washed with cyclohexane and dried.

70 g (69% of theory) of 1-chlorocarbonyl-3-dimethylamino-4-methyl-1,2,4-triazolin-5-one of melting point 78° C.–80° C. are obtained.

Example IV-1:

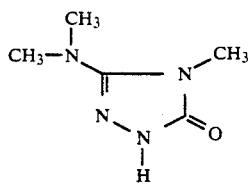

50 g (1.5 mol) of phosgene are passed into a suspension of 152.5 g (1 mol) of 1-amino-2,2,3-trimethylguanidinium hydrochloride in 1,000 ml of acetonitrile at 80° C. in the course of 2 hours, with stirring, the mixture is subsequently stirred at 80° C. for 30 minutes and cooled to 20° C., excess phosgene is removed by blowing out with nitrogen, the product which has precipitated is filtered off with suction and dissolved in 1,000 ml of water and the solution is neutralized with concentrated sodium hydroxide solution and concentrated to dryness in vacuo. The oily residue is taken up in 1,000 ml of acetonitrile, the mixture is filtered and the filtrate is freed from the solvent in vacuo.

80 g (57% of theory) of 3-dimethylamino-4-methyl-1H-1,2,4-triazolin-5-one of melting point 78° C.–80° C. are obtained.

Example VII-1:

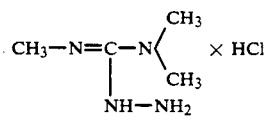

A solution of 78.5 g (0.5 mol) of chlorotrimethylformamidinium hydrochloride in 250 ml of isopropanol is added dropwise to 50 g (1 mol) of hydrazine hydrate in 300 ml of isopropanol at 20° C. to 25° C. in the course of 30 minutes, with stirring, when the addition has ended the mixture is stirred at room temperature for a further 30 minutes, the hydrazine hydrochloride which has precipitated is filtered off with suction and rinsed with 150 ml of isopropanol and the isopropanol filtrate is concentrated in vacuo.

70.7 g (93% of theory) of 1-amino-2,2,3-trimethylguanidinium hydrochloride are obtained and are further reacted without purification.

Example IX-1:

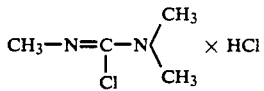

545 9 (5.5 mols) phosgene are passed into a mixture of 510 g (5 mols of N,N,N'-trimethylurea and 3 l of chlorobenzene at 80° C. in the course of 2.5 hours, with stirring, and when the introduction has ended the mixture is subsequently stirred at 80° C. for a further 45 minutes until the evolution of carbon dioxide has ended. The reaction mixture is cooled to 10° C. and the water-sensitive product is filtered off with suction under nitrogen, washed with 1 l of chlorobenzene and twice with 500 ml of petroleum ether each time and dried in vacuo.

635.3 g (81% of theory) of chlorotrimethylformamidinium hydrochloride of melting point 76° C. to 78° C. are obtained.

Example 2:

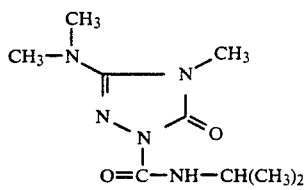

Process b 4.25 g (0.05 mol) of isopropyl isocyanate are added to 7.1 g (0.05 mol) of 3-dimethylamino-4-methyl-1H-1,2,4-triazolin-5-one in 100 ml of toluene and the mixture is stirred at 120° C. for 2 hours. The cooled reaction mixture is filtered and the filtrate is concentrated in vacuo.

9.8 g (87% of theory) of 1-isopropylaminocarbonyl-3-dimethylamino-4-methyl-1,2,4-triazolin-5-one of melting point 36° C.–38° C. are obtained.

Example 3:

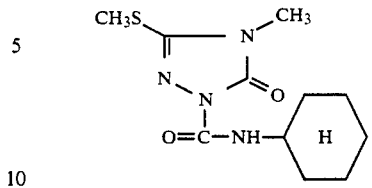

Process b 1 g (0.01 mol) of triethylamine and 1.3 g (0.01 mol) of cyclohexyl isocyanate are added to 1.5 g (0.01 mol) of 3-methylthio-4-methyl-1H-1,2,4-triazolin-5-one (compare U.S. Pat. No. 4,098,896 and U.S. Pat. No. 4,110,332) in 20 ml of dioxane, the mixture is stirred at 60° C. for 12 hours and concentrated to dryness in vacuo, the residue is taken up in 50 ml of methylene chloride, the mixture is filtered, the filtrate is washed twice with 50 ml of water each time and dried over sodium sulphate, the solvent is removed in vacuo and the residue is triturated with ether.

2.2 g (81% of theory) of 1-cyclohexylaminocarbonyl-3-methylthio-4-methyl-1,2,4-triazolin-5-one of melting point 136° C. are obtained.

The following substituted triazolinones of the general formula (I) are obtained in a corresponding manner and in accordance with the general statements on the preparation:

| Example No. | $R^1$ | $R^2$ | $-N\genfrac{}{}{0pt}{}{R^3}{R^4}$ | X | Y | Physical properties |
|---|---|---|---|---|---|---|
| 4 | $CH_3$ | $-N(CH_3)_2$ | $-N(C_2H_5)_2$ | O | O | mp. 61–64° C. |
| 5 | $CH_3$ | $-N(CH_3)_2$ | $-N\genfrac{}{}{0pt}{}{CH_3}{C_6H_5}$ | O | O | mp. 76–77° C. |
| 6 | $CH_3$ | $-N(CH_3)_2$ | $-N\genfrac{}{}{0pt}{}{CH_3}{CH_2-CH_2-CN}$ | O | O | $^1$H-NMR*): 2.8–2.9; 3.6–3.8 |
| 7 | $CH_3$ | $-N(CH_3)_2$ | $-N\genfrac{}{}{0pt}{}{CH_3}{C_6H_{11}}$ | O | O | mp. 82–83° C. |
| 8 | $CH_3$ | $-N(CH_3)_2$ | $-NH-C_6H_5$ | O | O | mp. 123–124° C. |
| 9 | $CH_3$ | $-N(CH_3)_2$ | $-NH-CH_3$ | O | O | mp. 80–81° C. |
| 10 | $CH_3$ | $-N(CH_3)_2$ | $-NH-C(CH_3)_3$ | O | O | $^1$H-NMR*): 1.4 |

-continued

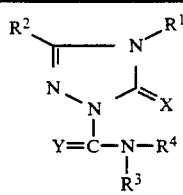
(I)

| Example No. | R¹ | R² | $-N\langle^{R^3}_{R^4}$ | X | Y | Physical properties |
|---|---|---|---|---|---|---|
| 11 | CH₃ | —N(CH₃)₂ | —NH—CO—C₆H₅ | O | O | mp. 183–184° C. |
| 12 | CH₃ | —N(CH₃)₂ | —NH—(3,4-Cl₂-C₆H₃) | O | O | mp. 159–160° C. |
| 13 | CH₃ | —N(CH₃)₂ | —N(CH₂CH₂CN)₂ | O | O | mp. 149–151° C. |
| 14 | CH₃ | —N(CH₃)₂ | —NH—cyclohexyl | O | O | mp. 91–93° C. |
| 15 | CH₃ | —N(CH₃)₂ | —NH—(CH₂)₅—CH₃ | O | O | mp. 91–93° C. |
| 16 | CH₃ | —N(CH₃)₂ | —NH₂ | O | O | mp. 161–162° C. |
| 17 | CH₃ | —N(CH₃)₂ | —NH—CH₂—C₆H₅ | O | O | mp. 65–67° C. |
| 18 | (CH₃)₂CH— | —N(CH₃)₂ | —NH—C(CH₃)₃ | O | O | ¹H-NMR*): 1.5; 4.1–4.2 |
| 19 | C₆H₅ | —N(CH₃)₂ | —NH—C(CH₃)₃ | O | O | mp. 132–134° C. |
| 20 | CH₃ | —N(CH₃)₂ | —NH—CH₂—CF₃ | O | O | mp. 78–80° C. |
| 21 | CH₃ | —N(CH₃)₂ | —NH—CH(CF₃)—CH₃ | O | O | mp. 101–103° C. |
| 22 | CH₃ | —N(CH₃)₂ | —NH—CH(CH₂F)₂ | O | O | mp. 79–81° C. |
| 23 | CH₃ | —N(CH₃)₂ | —NH—C(CH₃)₂—CH₂F | O | O | mp. 84–86° C. |
| 24 | CH₃ | —N(CH₃)₂ | —NH—(1-CH₃-2,2-F₂-cyclopropyl) | O | O | ¹H-NMR*): 1.5; 8.4 |

-continued

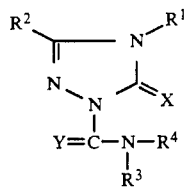
(I)

| Example No. | R¹ | R² | −N(R³)(R⁴) | X | Y | Physical properties |
|---|---|---|---|---|---|---|
| 25 | CH₃ | −N(CH₃)(cyclohexyl) | −NH−C(CH₃)₃ | O | O | ¹H-NMR*): 1.1–1.9; 3.0–3.1 |
| 26 | CH₃ | −N(CH₃)₂ | −NH−C(CH₃)₂−CH₂−C(CH₃)₃ | O | O | mp. 75–76° C. |
| 27 | CH₃ | −N(CH₂−CH=CH₂)₂ | −NH−C(CH₃)₃ | O | O | ¹H-NMR*): 1.4; 5.8–5.9 |
| 28 | CH₃ | −N(CH(CH₃)₂)₂ | −NH−C(CH₃)₃ | O | O | ¹H-NMR*): 1.1; 1.4; 3.4–3.5 |
| 29 | CH₃ | −N(C₂H₅)₂ | −NH−C(CH₃)₃ | O | O | ¹H-NMR*): 1.1–1.2; 1.4; 3.2 |
| 30 | CH₃ | −N(piperidinyl) | −NH−C(CH₃)₃ | O | O | mp. 57–58° C. |
| 31 | CH₃ | −N(CH₃)₂ | −NH−(CH₂)₂−Cl | O | O | mp. 58–59° C. |
| 32 | CH₃ | −N(CH₃)₂ | −NH−CH₂−cyclohexyl | O | O | ¹H-NMR*): 0.9–1.8; 3.2 |
| 33 | CH₃ | −N(CH₃)₂ | −NH−(CH₂)₃−N(CH₃)₂ | O | O | ¹H-NMR*): 1.7–1.8; 2.3–2.4; 3.4 |
| 34 | CH₃ | −N(CH₃)₂ | −NH−(CH₂)₁₁−CH₃ | O | O | mp. 46–48° C. |
| 35 | CH₃ | −N(CH₃)₂ | −NH−(3,3,5-trimethylcyclohexyl) | O | O | ¹H-NMR*): 0.9; 3.9 |
| 36 | CH₃ | −N(CH₃)₂ | −NH−(CH₂)₂−OCH₃ | O | O | ¹H-NMR*): 3.4; 3.5–3.6 |
| 37 | CH₃ | −N(CH₃)₂ | −NH−C(CH₃)₂−CH₂−OH | O | O | mp. 108–110° C. |

-continued

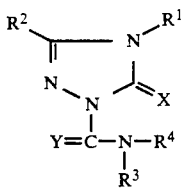
(I)

| Example No. | R[1] | R[2] | $-N\begin{smallmatrix}R^3\\R^4\end{smallmatrix}$ | X | Y | Physical properties |
|---|---|---|---|---|---|---|
| 38 | CH₃ | —N(CH₃)₂ | —NH—CH₂—(2-furyl) | O | O | mp. 115–117° C. |
| 39 | CH₃ | —N(CH₃)₂ | —NH—CH₂—CH(CH₃)₂ | O | O | mp. 57–59° C. |
| 40 | CH₃ | —N(CH₃)₂ | —NH—(CH₂)₃—N(morpholino) | O | O | ¹H-NMR*): 2.45; 3.7 |
| 41 | CH₃ | —N(CH₃)₂ | —NH—(2-methylphenyl) | O | O | mp. 126–128° C. |
| 42 | CH₃ | —N(CH₃)₂ | —NH—CH₂—CH(C₂H₅)(CH₂)₃—CH₃ | O | O | ¹H-NMR*): 0.9; 1.3–1.5; 3.45 |
| 43 | CH₃ | —N(CH₃)₂ | —NH—CH(CH₃)—C₂H₅ | O | O | ¹H-NMR*): 1.2; 3.9–3.95 |
| 44 | CH₃ | —N(CH₃)₂ | —NH—(2-hydroxyphenyl) | O | O | mp. 191–192° C. |
| 45 | CH₃ | —N(CH₃)₂ | —NH—(3-trifluoromethylphenyl) | O | O | mp. 94–96° C. |
| 46 | CH₃ | —N(CH₃)₂ | —NH—(4-nitrophenyl) | O | O | mp. 236–238° C. |
| 47 | CH₃ | —N(CH₃)₂ | —NH—(3-chloro-4-methylthiophenyl) | O | O | mp. 172–174° C. |
| 48 | CH₃ | —N(CH₃)₂ | —NH—(2-methylcyclohexyl) | O | O | ¹H-NMR*): 0.9–1.9 |

-continued

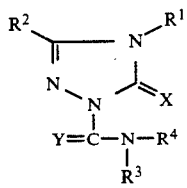
(I)

| Example No. | R¹ | R² | −N(R³)(R⁴) | X | Y | Physical properties |
|---|---|---|---|---|---|---|
| 49 | $CH_3$ | $-N(CH_3)_2$ | −NH−(2-Cl-C₆H₄) | O | O | mp. 139–140° C. |
| 50 | $CH_3$ | $-N(CH_3)_2$ | $-NH-CH_2-CH_2-C_6H_5$ | O | O | ¹H-NMR*): 7.1–7.3 |
| 51 | $CH_3$ | $-N(CH_3)_2$ | −NH−(2,6-(CH₃)₂-C₆H₃) | O | O | mp. 136–138° C. |
| 52 | $CH_3$ | $-N(CH_3)_2$ | −NH−(4-C(CH₃)₃-C₆H₄) | O | O | mp. 126–128° C. |
| 53 | $CH_3$ | $-N(CH_3)_2$ | $-NH-CH_2-C(CH_3)_3$ | O | O | mp. 72–73° C. |
| 54 | $CH_3$ | $-N(CH_3)_2$ | $-NH-CH(CH_3)-C(CH_3)_3$ | O | O | mp. 73–74° C. |
| 55 | $CH_3$ | $-N(CH_3)_2$ | $-NH-CH_2-C(CH_3)_2-CH_2-N(CH_3)_2$ | O | O | ¹H-NMR*): 2.2; 3.3 |
| 56 | $CH_3$ | $-N(CH_3)_2$ | $-NH-C(CH_3)(C_2H_5)(CH_3)$ | O | O | mp. 81–83° C. |
| 57 | $CH_3$ | $-N(CH_3)_2$ | $-NH-C(CH_2F)(CH_3)(CH_2F)$ | O | O | mp. 96–97° C. |
| 58 | $CH_3$ | $-N(CH_3)_2$ | $-NH-CH(CH_3)-C_6H_5$ | O | O | ¹H-NMR*): 7.2–7.3 |
| 59 | $CH_3$ | $-N(CH_3)_2$ | $-NH-(CH_2)_3-O-C_2H_5$ | O | O | ¹H-NMR*): 3.4–3.5 |
| 60 | $CH_3$ | $-N(CH_3)_2$ | −N(C₂H₅)−(2-CH₃-C₆H₄) | O | O | mp. 99–100° C. |

-continued

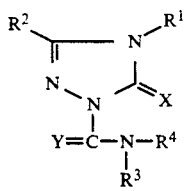

(I)

| Example No. | R¹ | R² | -N(R³)(R⁴) | X | Y | Physical properties |
|---|---|---|---|---|---|---|
| 61 | CH₃ | —N(CH₃)₂ | —N(CH₃)(CH(CH₃)₂) | O | O | ¹H-NMR*): 3.4–3.5 |
| 62 | CH₃ | —N(CH₃)₂ | —N(CH₃)(C(CH₃)₃) | O | O | ¹H-NMR*): 1.4; 2.95 |
| 63 | CH₃ | —N(CH₃)₂ | —N(pyrrolidinyl) | O | O | ¹H-NMR*): 1.9; 3.6–3.7 |
| 64 | CH₃ | —N(CH₃)₂ | —N(piperidinyl) | O | O | ¹H-NMR*): 1.6; 3.5 |
| 65 | CH₃ | —N(CH₃)₂ | —NH—C(CH₃)₂—CN | O | O | mp. 147–150° C. |
| 66 | CH₃ | —N(CH₃)₂ | —N(4-methylpiperazinyl) | O | O | ¹H-NMR*): 2.3; 2.5; 3.6 |
| 67 | CH₃ | —N(CH₃)₂ | —NH—(2,6-difluoro-3-cyanophenyl) | O | O | mp. 215–217° C. |
| 68 | CH₃ | —N(CH₃)₂ | —NH—(CH₂)₃—CH₃ | O | O | ¹H-NMR*): 3.35–3.45 |
| 69 | CH₃ | —N(CH₃)₂ | —NH—C(CH₂OH)₃ | O | O | mp. 163–165° C. |
| 70 | CH₃ | —N(CH₃)₂ | —N(CH₃)—C(CH₃)₂—CN | O | O | mp. 117–119° C. |
| 71 | CH₃ | —N(CH₃)₂ | —NH—C(CH₃)₂—CF₃ | O | O | mp. 57–59° C. |
| 72 | CH₃ | —N(CH₃)(CH(CH₃)₂) | —NH—C(CH₃)₃ | O | O | ¹H-NMR*): 3.5–3.6 |

-continued

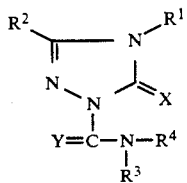  (I)

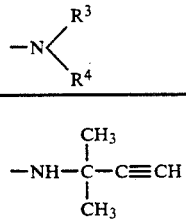

| Example No. | R¹ | R² | -N(R³)(R⁴) | X | Y | Physical properties |
|---|---|---|---|---|---|---|
| 73 | $CH_3$ | $-N(CH_3)_2$ | $-NH-C(CH_3)_2-C\equiv CH$ | O | O | mp. 115–117° C. |
| 74 | $CH_3$ | $-N(CH_3)(C_2H_5)$ | $-NH-C(CH_3)_3$ | O | O | ¹H-NMR*): 1.15–1.2; 3.5–3.6 |
| 75 | cyclohexyl | $N(CH_3)_2$ | $-NH-C(CH_3)_3$ | O | O | mp. 108–110° C. |
| 76 | $CH_3$ | $-N(CH_3)_2$ | $-NH-*CH(CH_3)-C_6H_5$ R(+) | O | O | mp. 80–82° C. |
| 77 | $CH_3$ | $-N(CH_3)_2$ | $-NH-*CH(CH_3)-C_6H_5$ S(−) | O | O | mp. 48–50° C. |
| 78 | $CH_3$ | $-N(CH_3)_2$ | $-NH-CH(CH_3)-$cyclohexyl | O | O | ¹H-NMR*): 3.85–3.95 |
| 79 | $CH_3$ | $-N(CH_3)_2$ | $-NH-CH(CH_3)-C_6H_4-F$ | O | O | ¹H-NMR*): 7.0; 7.35 |
| 80 | $CH_3$ | $-N(CH_3)_2$ | $-NH-CH(CH_3)-C_6H_4-Cl$ | O | O | ¹H-NMR*): 7.3 |
| 81 | $CH_3$ | $-N(CH_3)_2$ | $-NH-CH(CH_3)-C_6H_4-Br$ | O | O | ¹H-NMR*): 7.25; 7.45 |
| 82 | $CH_3$ | $-N(CH_3)_2$ | $-NH-CH((CH_2)_3-CH_3)-C_6H_5$ | O | O | ¹H-NMR*): 7.3 |
| 83 | $CH_3$ | $-N(CH_3)_2$ | $-NH-CH(CH_3)-CH_2-C_6H_4-CF_3$ | O | O | ¹H-NMR*): 4.3–4.4 |

-continued

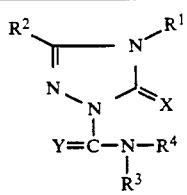

| Example No. | R¹ | R² | -N(R³)(R⁴) | X | Y | Physical properties |
|---|---|---|---|---|---|---|
| 84 | CH₃ | —N(CH₃)₂ | —N(CH₃)—CH(CH₃)—C₆H₅ | O | O | ¹H-NMR*): 5.6 |
| 85 | CH₃ | —N(CH₃)₂ | —NH—CH₂—(3,4-dimethylcyclohex-3-enyl) | O | O | ¹H-NMR*): 3.3–3.35 |
| 86 | CH₃ | —N(CH₃)₂ | —NH—CH₂—(3-methylcyclohex-3-enyl) | O | O | ¹H-NMR*): 3.3–3.35 |
| 87 | CH₃ | —N(CH₃)₂ | —NH—(3,5-dichlorophenyl) | O | O | mp. 181–182° C. |
| 88 | CH₃ | —N(CH₃)₂ | —NH—(4-chlorophenyl) | O | O | mp. 162–163° C. |
| 89 | CH₃ | —N(CH₃)₂ | —NH—(3-chlorophenyl) | O | O | mp. 103–105° C. |
| 90 | CH₃ | —N(CH₃)₂ | —NH—(3-nitrophenyl) | O | O | mp. 187–188° C. |
| 91 | CH₃ | —N(CH₃)₂ | —NH—(2-trifluoromethyl-4-chlorophenyl) | O | O | mp. 138–139° C. |
| 92 | CH₃ | —N(CH₃)₂ | —N(CH₃)—CH₂—C₆H₅ | O | O | ¹H-NMR*): 7.1–7.4 |

-continued

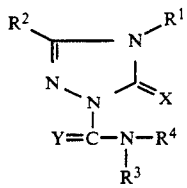
(I)

| Example No. | $R^1$ | $R^2$ | $-N\begin{matrix}R^3\\R^4\end{matrix}$ | X | Y | Physical properties |
|---|---|---|---|---|---|---|
| 93 | $CH_3$ | $-N(CH_3)_2$ | $-NH-\text{C}_6H_4-CO-CH_3$ (p-acetylphenyl) | O | O | mp. 181–182° C. |
| 94 | $CH_3$ | $-N(CH_3)_2$ | $-NH-CH(CH_2CH(CH_3)_2)(CH_2CH_2C_6H_5)$ | O | O | $^1$H-NMR*): 4.05–4.15 |
| 95 | $CH_3$ | $-N(CH_3)_2$ | $-NH-C_6H_4-C_6H_{11}$ (p-cyclohexylphenyl) | O | O | mp. 141–142° C. |
| 96 | $CH_3$ | $-N(CH_3)_2$ | $-NH-$ (3-chloro-6-phenoxyphenyl) | O | O | mp. 137–138° C. |
| 97 | $CH_3$ | $-N(CH_3)_2$ | $-NH-C(CH_3)(C_2H_5)(CN)$ | O | O | $^1$H-NMR*): 1.75; 3.0–2.1 |
| 98 | $CH_3$ | $-N(CH_3)_2$ | $-NH-C(CH_3)(CH(CH_3)_2)(CN)$ | O | O | $^1$H-NMR*): 1.1–1.2; 2.35 |
| 99 | $CH_3$ | $-N(CH_3)_2$ | $-NH-CH(C_6H_5)(CN)$ | O | O | mp. 117–119° C. |
| 100 | $CH_3$ | $-N(CH_3)_2$ | $-NH-C(CH_3)(C_6H_5)(CN)$ | O | O | $^1$H-NMR*): 7.3–7.6 |
| 101 | $CH_3$ | $-N(CH_3)_2$ | $-NH-$ cyclopropyl | O | O | mp. 92–93° C. |
| 102 | $CH_3$ | $-N(CH_3)_2$ | $-NH-C_2H_5$ | O | O | mp. 49–51° C. |
| 103 | $CH_3$ | $-N(CH_3)_2$ | $-NH-(CH_2)_2-CH_3$ | O | O | mp. 73–74° C. |
| 104 | cyclohexyl | $-N(CH_3)_2$ | $-NH-CH(CH_3)-C(CH_3)_3$ | O | O | $^1$H-NMR*): 3.15; 3.9 |

-continued

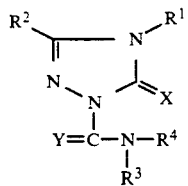

| Example No. | $R^1$ | $R^2$ | $-N\begin{smallmatrix}R^3\\R^4\end{smallmatrix}$ | X | Y | Physical properties |
|---|---|---|---|---|---|---|
| 105 | $CH_3$ | $-N(CH_3)(C_2H_5)$ | $-NH-CH(CH_3)-C(CH_3)_3$ | O | S | $^1$H-NMR*): 3.15; 3.85 |
| 106 | $CH_3$ | $-N(CH_3)_2$ | $-NH-CH(CH_3)-C(CH_3)_3$ | O | S | mp. 91–92° C. |
| 107 | $CH_3$ | $-N(CH_3)_2$ | $-NH-C(CH_3)_3$ | O | S | mp. 85–86° C. |
| 108 | $CH_3$ | $-N(CH_3)_2$ | $-NH-CH_2-CH=CH_2$ | O | S | mp. 87–89° C. |
| 109 | $CH_3$ | $-N(CH_3)_2$ | $-NH-CH_2-CN$ | O | O | mp. 124–125° C. |
| 110 | $CH_3$ | $-N(CH_3)_2$ | $-NH-C(CH_3)_2-CH_2Cl$ | O | O | mp. 70–72° C. |
| 111 | $CH_3$ | $-N(CH_3)_2$ | $-NH-C(CH_3)(CH_2Cl)_2$ | O | O | mp. 113–115° C. |
| 112 | $CH_3$ | $-N(CH_3)_2$ | $-NH-$(3-methylcyclohexyl) | O | O | mp. 60–61° C. |
| 113 | $CH_3$ | $-N(CH_3)_2$ | $-NH-$(4-methylcyclohexyl) | O | O | $^1$H-NMR*): 0.9; 7.8–8.2 |
| 114 | $CH_3$ | $-N(CH_3)_2$ | $-NH-C(CH_3)_2-CHCl_2$ | O | O | mp. 120–121° C. |
| 115 | $CH_3$ | $-N(CH_3)_2$ | $-NH-CH(CN)-CH(CH_3)_2$ | O | O | mp. 72–73° C. |
| 116 | $CH_3$ | $-N(CH_3)_2$ | $-NH-$(2-cyanocyclohexyl) | O | O | mp. 78–80° C. |
| 117 | $CH_3$ | $-N(CH_3)_2$ | $-NH-CH(CN)-C_6H_5$ | O | O | $^1$H-NMR*): 2.95; 6.65 |
| 118 | $CH_3$ | $-N(CH_3)(C_2H_5)$ | $-NH-(CH_2)_3-CH_3$ | O | O | $^1$H-NMR*): 7.9 |

-continued

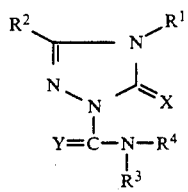
(I)

| Example No. | R¹ | R² |   -N(R³)(R⁴) | X | Y | Physical properties |
|---|---|---|---|---|---|---|
| 119 | CH₃ | —N(CH₃)₂ | —NH—CH₂—(3-pyridyl) | O | O | ¹H-NMR*): 7.3–8.5 |
| 120 | CH₃ | —N(CH₃)₂ | —NH—cyclopentyl | O | O | mp. 75–77° C. |
| 121 | CH₃ | —N(CH₃)₂ | —NH—cycloheptyl | O | O | mp. 58–59° C. |
| 122 | CH₃ | —N(CH₃)₂ | —NH—cyclooctyl | O | O | mp. 47–48° C. |
| 123 | CH₃ | —N(CH₃)₂ | —NH—CH(CH₃)—CH(CH₃)₂ | O | O | ¹H-NMR*): 3.85–3.95 |
| 124 | CH₃ | —N(CH₃)₂ | —NH—CH₂—CH(CH₃)—C₂H₅ | O | O | ¹H-NMR*): 7.9 |
| 125 | CH₃ | —N(CH₃)₂ | —NH—CH₂—CH₂—CH(CH₃)₂ | O | O | ¹H-NMR*): 7.8 |
| 126 | CH₃ | —N(CH₃)₂ | —NH—CH(CH₃)—CH₂—CH(CH₃)₂ | O | O | ¹H-NMR*): 7.8 |
| 127 | CH₃ | —N(CH₃)₂ | —NH—(CH₂)₃—C(CH₃)₃ | O | O | ¹H-NMR*): 7.9 |
| 128 | CH₃ | —N(CH₃)₂ | —NH—CH₂—(4-pyridyl) | O | O | ¹H-NMR*): 7.2–8.5 |
| 129 | CH₃ | —N(CH₃)₂ | —NH—CH(CN)—C(CH₃)₃ | O | O | mp. 99–101° C. |
| 130 | CH₃ | —N(CH₃)₂ | —NH—C(CN)(CH₃)—C(CH₃)₃ | O | O | mp. 167–168° C. |
| 131 | CH₃ | —N(CH₃)₂ | —NH—CH₂—(2-pyridyl) | O | O | mp. 109–111° C. |

-continued

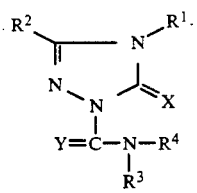
(I)

| Example No. | R¹ | R² | −N(R³)(R⁴) | X | Y | Physical properties |
|---|---|---|---|---|---|---|
| 132 | CH₃ | −N(CH₃)₂ | −NH−C(CH₃)(CH₃)−CH₂−CH₂−CH₃ | O | O | mp. 30–31° C. |
| 133 | CH₃ | −N(CH₃)₂ | −NH−CH₂−CH₂−CN | O | O | mp. 117–119° C. |
| 134 | CH₃ | −N(CH₃)₂ | −NH−*CH(CH₃)−C₆H₁₁  R(−) | O | O | ¹H-NMR*): 3.9 |
| 135 | CH₃ | −N(CH₃)₂ | −NH−*CH(CH₃)−C₆H₁₁  S(+) | O | O | ¹H-NMR*): 3.9 |
| 136 | CH₃ | −N(CH₃)₂ | −NH−O−CH₂−C₆H₅ | O | O | mp. 130° C. |
| 137 | CH₃ | −N(CH₃)₂ | −NH−O−CH(CH₃)₂ | O | O | mp. 103° C. |
| 138 | CH₃ | −N(CH₃)₂ | −NH−O−CH₂−CH(CH₃)₂ | O | O | ¹H-NMR*): 2.0; 3.8 |
| 139 | CH₃ | −N(CH₃)₂ | −NH−O−CH₂−CH=CH₂ | O | O | mp. 95° C. |
| 140 | CH₃ | −N(CH₃)₂ | −NH−O−(CH₂)₂−CH₃ | O | O | mp. 75° C. |
| 141 | CH₃ | −N(CH₃)₂ | −NH−CH(CH₃)−CN | O | O | mp. 102–104° C. |
| 142 | CH₃ | −SCH₃ | −NH−*CH(CH₃)−C₆H₅  S(−) | O | O | mp. 99° C. |
| 143 | CH₃ | −SCH₃ | −NH−CH(CH₃)₂ | O | O | mp. 92° C. |
| 144 | CH₃ | −SCH₃ | −NH−(CH₂)₂−OC₂H₅ | O | O | mp. 59° C. |
| 145 | CH₃ | −SCH₃ | −NH−CH₂−C(CH₃)₃ | O | O | mp. 105° C. |
| 146 | CH₃ | −SCH₃ | −NH−C(CH₃)₃ | O | O | mp. 108° C. |
| 147 | CH₃ | −SCH₃ | −NH−CH₂−C₆H₅ | O | O | mp. 131° C. |
| 148 | CH₃ | −SCH₃ | −NH−CH(CH₃)−C₂H₅ | O | O | mp. 79° C. |
| 149 | CH₃ | −SCH₃ | −NH−CH₂−CH(CH₃)₂ | O | O | mp. 65° C. |
| 150 | CH₃ | −SCH₃ | −NH−(CH₂)₅−CH₃ | O | O | mp. 53° C. |
| 151 | CH₃ | −SCH₃ | −NH−(CH₂)₂−OCH₃ | O | O | mp. 99° C. |
| 152 | CH₃ | −SCH₃ | −NH−(CH₂)₃−OCH₃ | O | O | mp. 67° C. |
| 153 | CH₃ | −SCH₃ | −NH−(CH₂)₂−CH₃ | O | O | mp. 59° C. |

-continued

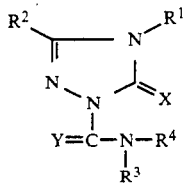
(I)

| Example No. | R¹ | R² | $-N\begin{smallmatrix}R^3\\R^4\end{smallmatrix}$ | X | Y | Physical properties |
|---|---|---|---|---|---|---|
| 154 | CH₃ | —SCH₃ | —N(morpholino) | O | O | mp. 111° C. |
| 155 | CH₃ | —SCH₃ | —NH—CH(CH₃)—C₆H₄—Cl (4-) | O | O | mp. 63° C. |
| 156 | CH₃ | —SCH₃ | —NH—CH(CH₃)—C₆H₄—Br (4-) | O | O | mp. 112° C. |
| 157 | CH₃ | —SCH₃ | —NH—CH(CH₃)—C₆H₄—F (4-) | O | O | mp. 115° C. |
| 158 | CH₃ | —SCH₃ | —NH—CH[(CH₂)₃—CH₃]—C₆H₅ | O | O | mp. 78° C. |
| 159 | CH₃ | —SCH₃ | —N(CH₃)—CH(CH₃)—C₆H₅ | O | O | ¹H-NMR*): 1.7; 4.5 |
| 160 | CH₃ | —SCH₃ | —NH—*CH(CH₃)—C₆H₅  R(+) | O | O | mp. 105° C. |
| 161 | CH₃ | —SCH₃ | —NH—CH₂—C₆H₄—Cl (4-) | O | O | mp. 217° C. |
| 162 | CH₃ | —N(CH₃)—CH₂—C₆H₅ | —NH—CH₃ | O | O | mp. 118–119° C. |
| 163 | CH₃ | —N(CH₃)₂ | —NH—C(CH₃)(cyclopropyl)(CN)H | O | O | mp. 204° C. (decomposition) |

-continued

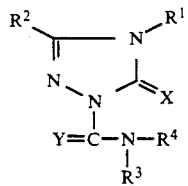
(I)

| Example No. | R¹ | R² | 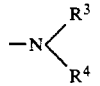 -N(R³)(R⁴) | X | Y | Physical properties |
|---|---|---|---|---|---|---|
| 164 | CH₃ | —N(CH₃)₂ | —NH—CH(CN)—(cyclohexenyl) | O | O | mp. 118–120° C. |
| 165 | CH₃ | —N(CH₃)₂ | —NH—CH(CN)—(CH₂)₂—C₆H₅ | O | O | mp. 110–112° C. |
| 166 | CH₃ | —N(CH₃)₂ | —NH—C(CH₂F)(CH₂F)(CH₂F) | O | O | mp. 110–112° C. |
| 167 | CH₃ | —N(CH₃)₂ | —NH—C₆H₅ | S | O | mp. 144–145° C. |
| 168 | CH₃ | —N(CH₃)₂ | —NH—cyclohexyl | S | O | mp. 90–91° C. |
| 169 | CH₃ | —N(CH₃)₂ | —NH—CH₂—C₆H₅ | S | O | mp. 67–68° C. |
| 170 | CH₃ | —N(CH₃)₂ | —NH—C(CH₂F)(CH₃)(CH₂F) | S | O | mp. 99–100° C. |
| 171 | CH₃ | CH₃S | —NH—cyclopentyl | O | O | mp. 122° C. |
| 172 | CH₃ | CH₃S | —N(CH₃)((CH₂)₃CH₃) | O | O | ¹H-NMR*): 3.1 (s) |
| 173 | CH₃ | CH₃S | —NH—(CH₂)₂—CH(CH₃)₂ | O | O | ¹H-NMR*): 0.9 (dd) |
| 174 | CH₃ | CH₃S | —NH—CH₂—CH(CH₃)—C₂H₅ | O | O | ¹H-NMR*): 1.7 (m) |
| 175 | CH₃ | CH₃S | —NH—(CH₂)₃—N(CH₃)₂ | O | O | ¹H-NMR*): 2.2 (s) |
| 176 | CH₃ | CH₃S | —NH—(CH₂)₄—CH₃ | O | O | ¹H-NMR*): 0.9 (t) |

-continued

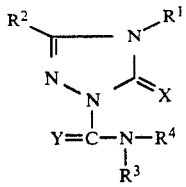
(I)

| Example No. | R¹ | R² | -N(R³)(R⁴) | X | Y | Physical properties |
|---|---|---|---|---|---|---|
| 177 | $CH_3$ | $CH_3S$ | —NH—(2-methylcyclohexyl) | O | O | mp. 97° C. |
| 178 | $CH_3$ | $CH_3S$ | —NH—(4-methylcyclohexyl) | O | O | mp. 157° C. |
| 179 | $CH_3$ | $CH_3S$ | —NH—$(CH_2)_2$—Cl | O | O | mp. 106° C. |
| 180 | $CH_3$ | $CH_3S$ | —NH—$(CH_2)_2$—(2-pyridyl) | O | O | mp. 85° C. |
| 181 | $CH_3$ | $CH_3S$ | —NH—(3-methylcyclohexyl) | O | O | ¹H-NMR*): 3.8 (m) |
| 182 | $CH_3$ | $CH_3S$ | —NH—$(CH_2)_2$—N(morpholino) | O | O | mp. 113° C. |
| 183 | $CH_3$ | $CH_3S$ | —NH—C($C_2H_5$)($CH_3$)($C_2H_5$) | O | O | mp. 112° C. |
| 184 | $CH_3$ | $CH_3S$ | —NH—$(CH_2)_2$—$C(CH_3)_3$ | O | O | mp. 79° C. |
| 185 | $CH_3$ | $CH_3S$ | —NH—C(CN)($CH_3$)($C(CH_3)_3$) | O | O | mp. 176° C. |
| 186 | $CH_3$ | $C_2H_5S$ | —NH—$CH(CH_3)_2$ | O | O | mp. 110° C. |
| 187 | $CH_3$ | $(CH_3)_2CHS$— | —NH—$CH(CH_3)_2$ | O | O | mp. 46° C. |
| 188 | $CH_3$ | $CH_3S$ | —NH—C($CH_2F$)($CH_3$)($CH_2F$) | O | O | mp. 121° C. |
| 189 | $CH_3$ | $CH_3S$ | —NH—CH($CH_3$)(cyclohexyl) | O | O | mp. 94° C. |

-continued

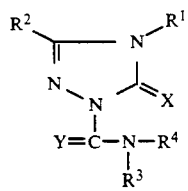

(I)

| Example No. | R¹ | R² | 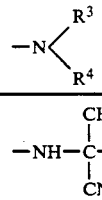 | X | Y | Physical properties |
|---|---|---|---|---|---|---|
| 190 | CH₃ | CH₃S | −NH−C(CH₃)(C₂H₅)−CN | O | O | mp. 131° C. |
| 191 | C₂H₅ | CH₃S | −NH−CH(CH₃)₂ | O | O | mp. 134° C. |
| 192 | CH₃ | CH₃S | −NH−CH(CN)−C(CH₃)₃ | O | O | mp. 144° C. |
| 193 | CH₃ | CH₃S | −NH−C(CH₃)(CN)−CH(CH₃)₂ | O | O | mp. 158° C. |
| 194 | CH₃ | (CH₃)₂N− | −NH−CH(CH(CH₃)₂)₂ | O | O | mp. 82–84 C. |
| 195 | CH₃ | (CH₃)₂N− | −NH(CH₂)₂−cyclohexenyl | O | O | mp. 57–59° C. |
| 196 | CH₃ | (CH₃)₂N− | −NH−CH(CH₂)(CH₂)(CH₂)₉ (cyclic) | O | O | mp. 114° C.–115° C. |
| 197 | CH₃ | (CH₃)₂N− | −NH−CH(CH₃)(CH₂)₂−C₆H₅ | O | O | ¹H-NMR*): 1.25; 1.85; 2.70; 4.05; 7.1–7.25 |
| 198 | CH₃ | (CH₃)₂N− | −NH−C(CH₃)(CN)−C₆H₄−Cl | O | O | mp. 46–47° C. |
| 199 | CH₃ | CH₃S | −NH−C(CH₃)(CH₃)−CH₂Cl | O | O | mp. 107° C.–109° C. |
| 200 | CH₃ | CH₃S | −NH−C(CH₃)₃ | O | O | mp. 119° C.–120° C. |
| 201 | CH₃ | CH₃S | −NH−CH(CN)−CH(CH₃)₂ | O | O | mp. 121° C.–123° C. |
| 202 | C₂H₅ | CH₃S | −NH−C(CH₃)(CH₃)−CH₂Cl | O | O | mp. 125° C.–127° C. |

-continued

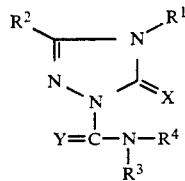
(I)

| Example No. | R¹ | R² | $-N\begin{smallmatrix}R^3\\R^4\end{smallmatrix}$ | X | Y | Physical properties |
|---|---|---|---|---|---|---|
| 203 | $C_2H_5$ | $CH_3S$ | $-NH-\underset{CH_2F}{\overset{CH_2F}{\underset{|}{C}}}-CH_3$ | O | O | mp. 79–81° C. |
| 204 | $C_2H_5$ | $CH_3S$ | $-NH-\underset{|}{\overset{CN}{CH}}-CH(CH_3)_2$ | O | O | mp. 81–83° C. |
| 205 | $C_2H_5$ | $CH_3S$ | $-NH-\triangle$ | O | O | mp. 68–69° C. |
| 206 | $C_2H_5$ | $CH_3S$ | $-NH-\underset{CN}{\overset{CH_3}{\underset{|}{C}}}-C_2H_5$ | O | O | mp. 86–87° C. |
| 207 | $C_2H_5$ | $CH_3S$ | $-NH-\underset{|}{\overset{CN}{CH}}-CH(CH_3)_2$ | O | O | mp. 86–88° C. |
| 208 | $C_2H_5$ | $CH_3S$ | $-NH-\underset{CH_3}{\overset{CN}{\underset{|}{C}}}-\triangle$ | O | O | mp. 140° C.–143° C. |
| 209 | $CH_3$ | $(CH_3)_2-N$ | $-NH-OCH_3$ | O | O | mp. 109° C.–112° C. |
| 210 | $CH_3$ | $(CH_3)_2N-$ | $-NH-CH_2-CH\underset{OCH_3}{\overset{OCH_3}{<}}$ | O | O | ¹H-NMR*): 2.90; 3,50; 4.45 |
| 211 | $CH_3$ | $C_2H_5-S-$ | $-NH-CH_3$ | O | O | mp. 137° C.–139° C. |
| 212 | $C_2H_5$ | $CH_3S$ | $-NH-CH_3$ | O | O | mp. 159° C.–160° C. |
| 213 | $C_2H_5$ | $C_2H_5S-$ | $-NH-CH_3$ | O | O | mp. 122° C.–123° C. |
| 214 | $C_2H_5$ | $-S-CH_2-C_6H_5$ | $-NH-CH_3$ | O | O | mp. 126° C.–127° C. |
| 215 | $CH_3$ | $-S-CH_2-CH=CH_2$ | $-NH-C(CH_3)_3$ | O | O | mp. 126° C.–127° C. |
| 216 | $CH_3$ | $-S-C_2H_5$ | $NH-CH_2-C(CH_3)_3$ | O | O | mp. 86–87° C. |
| 217 | $CH_3$ | $-S-CH_2-C_6H_5$ | $-NH-CH_2-C(CH_3)_3$ | O | O | mp. 144° C.–148° C. |
| 218 | $C_2H_5$ | $-S-CH_3$ | $-NH-CH_2-C(CH_3)_3$ | O | O | mp. 143° C.–145° C. |
| 219 | $C_2H_5$ | $-S-C_2H_5$ | $-NH-CH_2-C(CH_3)_3$ | O | O | mp. 72–73° C. |

-continued

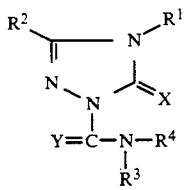
(I)

| Example No. | $R^1$ | $R^2$ | $-N\begin{matrix}R^3\\R^4\end{matrix}$ | X | Y | Physical properties |
|---|---|---|---|---|---|---|
| 220 | $C_2H_5$ | $-S-CH_2-C_6H_5$ | $-NH-CH_2-C(CH_3)_3$ | O | O | mp. 80–81° C. |
| 221 | $CH_3$ | $-S-C_2H_5$ | $-NH-$ cyclohexyl (H) | O | O | mp. 137° C.–138° C. |
| 222 | $CH_3$ | $-S-C_2H_5$ | $-NH-$(2-Cl-C_6H_4) | O | O | mp. 133° C.–134° C. |
| 223 | $C_2H_5$ | $-S-CH_3$ | $-NH-$ cyclohexyl (H) | O | O | mp. 119° C.–120° C. |
| 224 | $C_2H_5$ | $-S-C_2H_5$ | $-NH-$ cyclohexyl (H) | O | O | mp. 115° C.–116° C. |
| 225 | $C_2H_5$ | $-S-CH_2-C_6H_5$ | $-NH-$ cyclohexyl (H) | O | O | mp. 95–96° C. |
| 226 | $CH_3$ | $-S-CH_2-C_6H_5$ | $-NH-CH(CH_3)-C_6H_5$ | O | O | mp. 112° C.–113° C. |
| 227 | $C_2H_5$ | $-S-CH_3$ | $-NH-CH(CH_3)-C_6H_5$ | O | O | mp. 99–100° C. |
| 228 | $C_2H_5$ | $-S-C_2H_5$ | $-NH-CH(CH_3)-C_6H_5$ | O | O | mp. 84–85° C. |
| 229 | $CH_3$ | $-S-CH_2-C_6H_5$ | $-NH-CH_3$ | O | O | mp. 125° C.–127° C. |
| 230 | $CH_3$ | $-S-C_2H_5$ | $-N$(morpholino) | O | O | $^1$H-NMR*): 3.17 (s) |

-continued

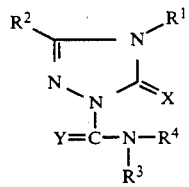
(I)

| Example No. | R¹ | R² | -N(R³)(R⁴) | X | Y | Physical properties |
|---|---|---|---|---|---|---|
| 231 | $C_2H_5$ | $-S-C_2H_5$ | -N(morpholino, O in ring) | O | O | ¹H-NMR*): 3.20 (q); 1.43 (t); 1.22 (t) |
| 232 | $CH_3$ | $-S-C_2H_5$ | -N(pyrrolidino) | O | O | ¹H-NMR*): 3.18 (s); 1.43 (t) |
| 233 | $CH_3$ | $-S-C_2H_5$ | $-NH-C(CH_3)_2-C_2H_5$ | O | O | mp. 100° C.-101° C. |
| 234 | $C_2H_5$ | $-S-CH_2-CH=CH_2$ | $-NH-C(CH_3)_3$ | O | O | mp. 75-77° C. |
| 235 | $C_2H_5$ | $-S-CH_2-CH=CH_2$ | $-NH-CH_3$ | O | O | mp. 84-86° C. |
| 236 | $CH_3$ | $-S-CH_2-CH=CH_2$ | -NH-cyclopentyl | O | O | mp. 95-97° C. |
| 237 | $CH_3$ | $-S-CH_2-CH=CH_2$ | $-NH-CH_2-C(CH_3)_3$ | O | O | mp. 84-86° C. |
| 238 | $CH_3$ | $-S-CH_2-CH=CH_2$ | -NH-cyclohexyl | O | O | mp. 154° C.-155° C. |
| 239 | $CH_3$ | $-S-CH_2-CH=CH_2$ | -NH-cyclopropyl | O | O | mp. 86-87° C. |
| 240 | $CH_3$ | $-S-CH_2-CH=CH_2$ | $-NH-CH_2-CH=CH_2$ | O | O | ¹H-NMR*): 3.22 (s); 3.85 (d) |
| 241 | $CH_3$ | $-S-CH_2-CH=CH_2$ | -NH-(2-chlorophenyl) | O | O | mp. 132° C.-134° C. |
| 242 | $-CH_2-C_6H_5$ | $-S-CH_3$ | -NH-cyclopentyl | O | O | ¹H-NMR*): 2.60 (s); 4.77 (s) |
| 243 | $C_2H_5$ | $-S-C_2H_5$ | -N(piperidino) | O | O | ¹H-NMR*): 1.27 (t); 1.42 (t); 3.19 (q); |
| 244 | $CH_3$ | $-S-CH_2-CH=CH_2$ | $-N(CH_2-CH=CH_2)_2$ | O | O | ¹H-NMR*): 3.2 (s); 3.78 (d); 4.00 (d) |
| 245 | $C_2H_5$ | $-S-CH_2-CH=CH_2$ | $-NH-CH_2-C(CH_3)_3$ | O | O | ¹H-NMR*): 3.90 (d); |

-continued $$\text{(I)}$$

[Structure: 1,2,4-triazoline ring with R¹ on N, R² on C=N, X double-bonded to C, Y=C-N(R³)(R⁴) substituent]

| Example No. | R¹ | R² | -N(R³)(R⁴) | X | Y | Physical properties |
|---|---|---|---|---|---|---|
|  |  |  |  |  |  | 3.72 (q); 3.20 (d); 1.30 (t) |
| 246 | C₂H₅ | —S—CH₂—CH=CH₂ | —NH—(cyclohexyl) H | O | O | mp. 132° C.–134° C. |
| 247 | C₂H₅ | —S—CH₂—CH=CH₂ | —NH—(cyclopropyl) | O | O | ¹H-NMR*): 3.89 (d); 3.68 (q); 2.80 (m); 1.28 (t) |
| 248 | CH₃ | —S—CH₂—CH=CH₂ | —N(morpholino) | O | O | ¹H-NMR*): 3.19 (s); 3.84 (d) |
| 249 | CH₃ | —S—CH₂—CH=CH₂ | —NH—CH(CH₃)—C₂H₅ | O | O | mp. 84–85° C. |
| 250 | CH₃ | —S—CH₂—CH=CH₂ | —NH—C(CH₃)₂—C₂H₅ | O | O | mp. 87–89° C. |
| 251 | —CH₂—C₆H₅ | —SCH₃ | —NH—(2-Cl-C₆H₄) | O | O | mp. 156° C.–158° C. |
| 252 | CH₃ | —S—CH₂—C₆H₅ | —NH—CH(CH₃)—C₂H₅ | O | O | mp. 125° C.–127° C. |
| 253 | CH₂ | —S—CH₂—C₆H₅ | —NH—C(CH₃)₂—C₂H₅ | O | O | mp. 145° C.–147° C. |
| 254 | CH₃ | —S—CH₂—C₆H₅ | —NH—CH₂—CH=CH₂ | O | O | mp. 93–94° C. |
| 255 | CH₃ | —S—CH₂—C₆H₅ | —N(CH₂—CH=CH₂)₂ | O | O | ¹H-NMR*): 3.07 (s); 4.33 (s) |
| 256 | CH₃ | —S—CH₂—C₆H₅ | —N(morpholino) | O | O | mp. 113° C.–115° C. |

-continued

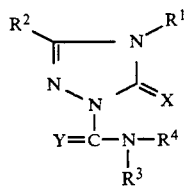
(I)

| Example No. | R¹ | R² | $-N\overset{R^3}{\underset{R^4}{\diagdown}}$ | X | Y | Physical properties |
|---|---|---|---|---|---|---|
| 257 | CH₃ | −S−CH₂−C₆H₅ | −NH−(2-Cl-C₆H₄) | O | O | mp. 163° C.–165° C. |
| 258 | C₂H₅ | −S−CH(CH₃)₂ | −NH−CH₃ | O | O | mp. 82–84° C. |
| 259 | CH₃ | −S−C₂H₅ |  (piperidinyl) | O | O | ¹H-NMR*): 3.16 (s); 1.42 (t) |
| 260 | C₂H₅ | −S−CH(CH₃)₂ | −NH−C(CH₃)₃ | O | O | mp. 78–79° C. |
| 261 | C₂H₅ | −S−CH(CH₃)₂ | −NH−CH₂−C(CH₃)₃ | O | O | mp. 61–62° C. |
| 262 | C₂H₅ | −S−CH(CH₃)₂ | −NH−cyclopropyl | O | O | mp. 88–89° C. |
| 263 | C₂H₅ | −S−CH(CH₃)₂ | −NH−cyclopentyl | O | O | mp. 48–50° C. |
| 264 | C₂H₅ | −S−CH(CH₃)₂ | −NH−cyclohexyl | O | O | mp. 53–55° C. |
| 265 | C₂H₅ | −S−CH(CH₃)₂ | −NH−(2-Cl-C₆H₄) | O | O | mp. 120° C.–122° C. |
| 266 | C₂H₅ | −S−CH(CH₃)₂ | −NH−CH(CH₃)−C₆H₅ | O | O | mp. 72–75° C. |
| 267 | cyclopropyl | −S−CH₃ | −NH−C(CH₃)₃ | O | O | mp. 174° C.–175° C. |
| 268 | cyclopropyl | −S−CH₃ | −NH−CH₂−C(CH₃)₃ | O | O | mp. 111° C.–113° C. |
| 269 | cyclopropyl | −S−CH₃ | −NH−cyclopropyl | O | O | mp. 113° C.–114° C. |
| 270 | cyclopropyl | −S−CH₃ | −NH−cyclopentyl | O | O | mp. 135° C.–137° C. |

-continued

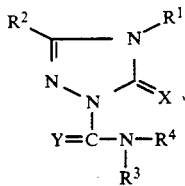  (I)

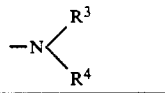

| Example No. | R¹ | R² | −N(R³)(R⁴) | X | Y | Physical properties |
|---|---|---|---|---|---|---|
| 271 | cyclopropyl | −S−CH₃ | −NH−cyclohexyl | O | O | mp. 107° C.–108° C. |
| 272 | cyclopropyl | −S−CH₃ | −NH−(2-Cl-C₆H₄) | O | O | mp. 152° C.–154° C. |
| 273 | cyclopropyl | −S−CH₃ | −NH−CH(CH₃)−C₆H₅ | O | O | mp. 124° C.–125° C. |
| 274 | −CH₂−C₆H₅ | −S−CH₃ | −NH−CH₃ | O | O | mp. 154° C.–156° C. |
| 275 | C₂H₅ | −SC₂H₅ | −N(piperidino) | O | O | ¹H-NMR*): 1.26 (t); 3.65 (q); 1.42 (t); 3.19 (q) |
| 276 | −CH₂−C₆H₅ | −S−CH₃ | −NH−CH(CH₃)−C₂H₅ | O | O | mp. 60–62° C. |
| 277 | −CH₂−C₆H₅ | −S−CH₃ | −NH−C(CH₃)₃ | O | O | mp. 67–70° C. |
| 278 | −CH₂−C₆H₅ | −S−CH₃ | −NH−CH₂−C(CH₃)₃ | O | O | mp. 79–81° C. |
| 279 | −CH₂−C₆H₅ | −S−CH₃ | −NH−C(CH₃)₂−C₂H₅ | O | O | mp. 68–71° C. |
| 280 | −CH₂−C₆H₅ | −S−CH₃ | −NH−CH₂−CH=CH₂ | O | O | mp. 80–82° C. |
| 281 | −CH₂−C₆H₅ | −S−CH₃ | −N(CH₂−CH=CH₂)₂ | O | O | ¹H-NMR*): 2.51 (s); 4.74 (s) |

-continued

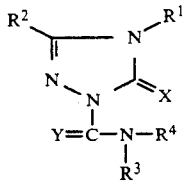
(I)

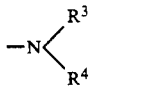

| Example No. | R¹ | R² | —NR³R⁴ | X | Y | Physical properties |
|---|---|---|---|---|---|---|
| 282 | —CH₂—C₆H₅ | —S—CH₃ | —NH-cyclopropyl | O | O | mp. 117° C.–118° C. |
| 283 | —CH₂—C₆H₅ | —S—CH₃ | —NH-cyclohexyl | O | O | mp. 89–91° C. |
| 284 | —CH₂—C₆H₅ | —S—CH₃ | -morpholino (—N(CH₂CH₂)₂O) | O | O | mp. 120° C.–121° C. |
| 285 | CH₃ | C₆H₅—CH₂—S— | —NH-cyclohexyl | O | O | mp. 178° C.–179° C. |
| 286 | CH₃ | (CH₃)₂CH—S— | —NH-cyclohexyl | O | O | mp. 63–69° C. |
| 287 | CH₃ | (CH₃)₂CH—S— | —NH—C(CH₃)₃ | O | O | mp. 86–87° C. |
| 288 | CH₃ | (CH₃)₂CH—S— | —NH-cyclopentyl | O | O | mp. 59–61° C. |
| 289 | CH₃ | (CH₃)₂CH—S— | —NH—CH(CH₃)—C₆H₅ | O | O | mp. 62–64° C. |
| 290 | CH₃ | (CH₃)₂CH—S— | —NH—CH₂—C(CH₃)₃ | O | O | mp. 72–74° C. |
| 291 | CH₃ | (CH₃)₂—S— | —NH-cyclopropyl | O | O | mp. 93–94° C. |
| 292 | CH₃ | (C₂H₅—S— | —NH-cyclopropyl | O | O | mp. 112° C.–113° C. |
| 293 | CH₃ | C₆H₅—CH₂—S— | —NH-cyclopropyl | O | O | mp. 141° C.–143° C. |
| 294 | C₂H₅ | C₂H₅—S— | —NH-cyclopropyl | O | O | mp. 84–85° C. |

-continued

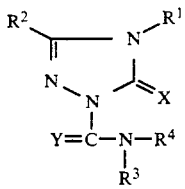
(I)

$-N\begin{cases}R^3\\R^4\end{cases}$ 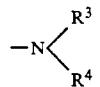

| Example No. | R¹ | R² | $-N\begin{cases}R^3\\R^4\end{cases}$ | X | Y | Physical properties |
|---|---|---|---|---|---|---|
| 295 | $C_2H_5$ | C₆H₅—CH₂—S— | —NH—cyclopropyl | O | O | mp. 130° C.–131° C. |
| 296 | $CH_3$ | $C_2H_5$—S— | —NH—C(CH₃)₃ | O | O | mp. 123° C.–124° C. |
| 297 | $CH_3$ | C₆H₅—CH₂—S— | —NH—C(CH₃)₃ | O | O | mp. 176° C.–177° C. |
| 298 | $C_2H_5$ | $CH_3$—S— | —NH—C(CH₃)₃ | O | O | mp. 111° C.–112° C. |
| 299 | $C_2H_5$ | $C_2H_5$—S— | —NH—C(CH₃)₃ | O | O | mp. 85–87° C. |
| 300 | $C_2H_5$ | C₆H₅—CH₂—S— | —NH—C(CH₃)₃ | O | O | mp. 151° C.–152° C. |
| 301 | $CH_3$ | $C_2H_5$—S— | —NH—cyclopentyl | O | O | mp. 114° C.–116° C. |
| 302 | $CH_3$ | C₆H₅—CH₂—S— | —NH—cyclopentyl | O | O | mp. 154° C.–155° C. |
| 303 | $C_2H_5$ | $CH_3$—S— | —NH—cyclopentyl | O | O | mp. 93–94° C. |
| 304 | $C_2H_5$ | $C_2H_5$—S— | —NH—cyclopentyl | O | O | mp. 74–75° C. |
| 305 | $C_2H_5$ | C₆H₅—CH₂—S— | —NH—cyclopentyl | O | O | mp. 75–77° C. |
| 306 | $CH_3$ | $C_2H_5$—S— | —NH—CH(CH₃)—C₆H₅ | O | O | mp. 105° C.–106° C. |
| 307 | $C_2H_5$ | C₆H₅—CH₂—S— | —NH—CH(CH₃)—C₆H₅ | O | O | mp. 88–89° C. |
| 308 | $C_2H_5$ | $CH_2=CH-CH_2$—S— | —NH—cyclopentyl | O | O | Resin ¹H-NMR*): 3.84 (d); 7.51 (d) |

-continued $$(I)$$

| Example No. | $R^1$ | $R^2$ | $-N\begin{smallmatrix}R^3\\R^4\end{smallmatrix}$ | X | Y | Physical properties |
|---|---|---|---|---|---|---|
| 309 | $C_2H_5$ | $CH_2=CH-CH_2-S-$ | $-NH-CH(CH_3)-C_6H_5$ | O | O | oil $^1$H-NMR*): 1.56 (d) 8.33 (d) 3.82 (d) |
| 310 | $CH_3$ | $CH_2=CH-CH_2-S-$ | $-NH-CH(CH_3)-C_6H_5$ | O | O | oil $^1$H-NMR*): 1.57 (d) 8.32 (d) 3.17 (s) 3.81 (d) |
| 311 | $CH_3$ | $CH_2=CH-CH_2-S-$ | $-NH-CH_3$ | O | O | mp. 95–97° C. |
| 312 | $CH_2-C_6H_5$ | $CH_3-S$ | $-NH-CH(CH_3)-C_6H_5$ | O | O | Resin $^1$H-NMR*): 1.57 (d); 2.55 (s); 4.73 (s) |
| 313 | $CH_3$ | $C_2H_5-S-$ | $-N$(piperidinyl) | O | O | mp. 74–75° C. |
| 314 | $C_2H_5$ | $C_2H_5-S-$ | $-N$(piperidinyl) | O | O | mp. 53–55° C. |

*)The $^1$H-NMR spectra were recorded in CDCl$_3$ with tetramethylsilane (TMS) as the internal standard. The chemical shift as the δ value in ppm is stated.

USE EXAMPLES

The compounds shown below were employed as comparison substances in the use examples which follow:

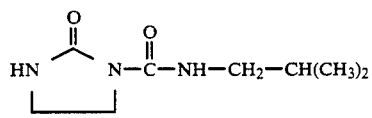

(A)

Imidazolidin-2-one-1-carboxylic acid isobutylamide (known from K.H. Büchel, "Pflanzenschutz und Schädlings-bekämpfung" ("Plant protection and pest control") page 170, Thieme Verlag Stuttgart 1977)

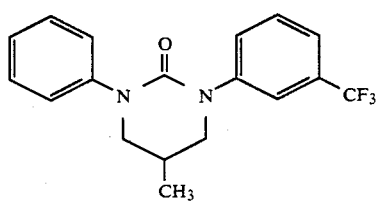

(B)

1Phenyl-3-(3-trifluoromethylphenyl)-5-methylperhydropyrimidin-2-one (known from European Patent 58,868)

Example A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the following compounds according to the invention exhibit a clearly superior activity compared with the prior art: 2, 10, 14, 39, 43, 48, 53, 54, 56, 57, 58, 65, 68 and 71.

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example, the following compounds according to the invention exhibit a clearly superior activity compared with the prior art 1, 2, 10, 14, 17, 32, 34, 36, 37, 39, 43, 50, 53, 54, 56, 57, 58, 65 and 68.

Example C

Defoliation and desiccation of the leaves of cotton

Solvent: 30 parts by weight of dimethylformamide
Emulsifier: 1 part by weight of polyoxyethylene sorbitane monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

The figures of merit have the following meanings 0 denotes no desiccation of leaves, no shedding of leaves + denotes slight desiccation of the leaves, slight shedding of leaves ++ denotes severe desiccation of the leaves, severe shedding of leaves +++ denotes very severe desiccation of the leaves, very severe shedding of leaves.

In this test, for example, the following compounds according to the invention exhibit a clearly superior activity compared with the untreated control: 15, 17, 32, 43, 48, 54, 56, 57 and 58.

It will be appreciated that the instant specification and claims are set forth by way of illustration and not limitation, and that various modifications and changes may be made without departing from the spirit and scope of the present invention.

We claim:

1. A compound of the formula

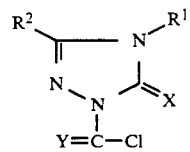

in which $R^1$ represents hydrogen, or represents in each case straight-chain or branched alkyl with 1 to 8 carbon atoms, alkenyl with 2 to 8 carbon atoms, alkinyl with 2 to 8 carbon atoms, halogenoalkyl with 1 to 8 carbon atoms and 1 to 17 identical or different halogen atoms, halogenoalkenyl with 2 to 8 carbon atoms and 1 to 15 identical or different halogen atoms, halogenolalkinyl with 2 to 8 carbon atoms and 1 to 13 identical or different halogen atoms or alkoxyalkyl or alkoxy with in each case 1 to 6 carbon atoms in the individual alkyl parts, or represents cycloalkyl-alkyl or cycloalkyl with in each case 3 to 7 carbon atoms in the cycloalkyl part and if appropriate 1 to 6 carbon atoms in the straight-chain or branched alkyl part, or represents aralkyl or aryl with in each case 6 to 10 carbon atoms in the aryl part and where appropriate 1 to 6 carbon atoms in the straight-chain or branched alkyl part, in each case optionally monosubstituted or polysubstituted in the aryl part by identical or different substituents from the group consisting of halogen, cyano, nitro and straight-chain or branched alkyl, alkoxy, alkylthio, halogenoalkyl, halogenolakoxy and halogenoalkylthio with carbon atoms and where appropriate 1 to 9 identical or different halogen atoms, $R^2$ represents a radical

or represents a radical $—S(O)_n—R^7$,

X represents oxygen or sulphur and

Y represents oxygen or sulphur, wherein $R^5$ and $R^6$ independently of one another each represent in each case straight-chain or branched alkyl with 1 to 8 carbon atoms, alkenyl with 2 to 8 carbon atoms, alkinyl with 2 to 8 carbon atoms, halogenoalkyl with 1 to 8 carbon atoms and 1 to 17 identical or different halogen atoms, halogenoalkenyl with 2 to 8 carbon atoms and 1 to 15 identical or different halogen atoms or halogenoalkinyl with 2 to 8 carbon atoms and 1 to 13 identical or different halogen atoms or alkoxyalkyl or alkoxy with in each case 1 to 6 carbon atoms in the individual alkyl parts, or represent cycloalkyl with 3 to 7 carbon atoms, or represent cycloalkylalkyl with 3 to 7 carbon atoms in the cycloalkyl part and 1 to 6 carbon atoms in the alkyl part, or represent aralkyl with 6 to 10 carbon atoms in the aryl part and 1 to 6 carbon atoms in the alkyl part and aryl with 6 to 10 carbon atoms optionally monosubstituted or polysubstituted by identical or different substituents from the group consisting of halogen, cyano, nitro and straight-chain or branched alkyl, alkoxy, alkylthio, halogenoalkyl, halogenoalkoxy or halogenoalkylthio with carbon atoms and where appropriate 1 to 9 identical or different halogen atoms, R⁷ represents in each case straight-chain or branched alkyl with 1 to 8 carbon atoms, alkenyl with 2 to 8 carbon atoms or alkinyl with 2 to 8 carbon atoms, or represents cycloalkyl with 3 to 7 carbon atoms,, or represents cycloalkylalkyl with 3 to 7 carbon atoms in the cycloalkyl part and 1 to 6 carbon atoms in the alkyl part, or represents aralkyl with 6 to 10 carbon atoms in the aryl part and 1 to 6 carbon atoms in the alkyl part or aryl with 6 to 10 carbon atoms, optionally monosubstituted or polysubstituted in the aryl part by identical or different substituents from the group consisting of halogen, cyano, nitro and chain or branched alkyl, alkoxy or halogenoalkyl with 1 to 4 carbon atoms and where appropriate 1 to 9 identical or different halogen atoms, and n represents the number 0, 1 or 2.

2. A compound according to claim 1, in which

R¹ represents hydrogen, methyl, ethyl, n- or i-propyl, n-, i-, s- or t-butyl, n- or i-pentyl, n- or i-hexyl, allyl, or represents straight-chain or branched halogenoalkyl with 1 to 4 carbon atoms and 1 to 9 identical or different halogen atoms, or represents cyclopentyl, cyclohexyl, cyclopropyl, cyclopropylmethyl, cyclohexylmethyl or cyclohexylethyl, or represents phenyl or benzyl, optionally substituted by one to three identical or different substituents from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy and trifluoromethylthio, R² represents a radical

or represents a radical —S(O)ₙ—R⁷,

X represents oxygen or sulphur and

Y represents oxygen or sulphur, wherein

R⁵ and R⁶ independently of one another each represent methyl, ethyl, n- or i-propyl, n-, i-, s- or t-butyl, n- or i-pentyl, allyl or propargyl, or represent in each case straight-chain or branched halogenoalkyl with 1 to 4 carbon atoms, halogenoalkenyl with 3 to 6 carbon atoms or halogenoalkinyl with 3 to 6 carbon atoms and 1 to 9 identical or different halogen atoms, or represent methoxymethyl, methoxyethyl, methoxy or ethoxy, or represent cyclopropyl, cyclopropylmethyl, cyclopentyl, cyclohexyl, cyclohexylmethyl, cyclohexylethyl or cyclopentylmethyl, or represent benzyl, phenethyl or phenyl, optionally substituted by one to three identical or different substituents from the group consisting of fluorine, chlorine, bromine, cyano, nitro, methyl, ethyl, n- oir i-propyl, n-, i-, s- or t-butyl, methoxy, ethoxy, methylthio, trifluoromethyl, trifluoromethoxy and trifluoromethylthio, R⁷ represents methyl, ethyl, n- or i-propyl, n-, i-, s- or t-butyl, allyl, propargyl, cyclopentyl, cyclohexyl, cyclohexylmethyl or cyclohexylethyl, or represents benzyl or phenyl, optionally substituted by one to three identical or different substituents from the group consisting of fluorine, chlorine, bromine, cyano, nitro, methyl, ethyl, n- or i-propyl, n-, i-, s- or t-butyl, methoxy, ethoxy and trifluoromethyl, and n represents the number 0, 1 or 2.

3. A compound according to claim 1, of the formula

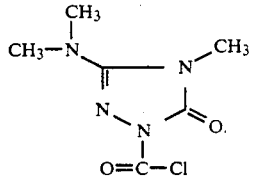

* * * * *

UNITED STATES PATENT AND TRADEMARK OFFICE
CERTIFICATE OF CORRECTION

PATENT NO. : 5,166,356
DATED : November 24, 1992
INVENTOR(S) : Findeisen et al.

It is certified that error appears in the above-identified patent and that said Letters Patent is hereby corrected as shown below:

| | | |
|---|---|---|
| Title Page | ABSTRACT: | Line 25 before " X " delete " pO "; line 26 before " Y " delete " pO " |
| Title Page | ABSTRACT: | Line 37 after " alkenyl " insert -- alkinyl -- |
| Col. 70, line 37 | | After " with " insert -- 1 to 4 -- |
| Col. 71, line 6 | | After " with " insert -- 1 to 4 -- |
| Col. 71, line 26 | | Before " chain " insert -- straight -- |
| Col. 71, line 35 | | After " allyl, " insert -- propargyl, methoxy, ethoxy or methoxymethyl, -- |
| Col. 72, line 26 | | Delete " oir " and substitute -- or -- |

Signed and Sealed this

Third Day of May, 1994

Attest:

BRUCE LEHMAN

*Attesting Officer*     *Commissioner of Patents and Trademarks*